(12) United States Patent
Schwenninger et al.

(10) Patent No.: US 7,927,639 B2
(45) Date of Patent: Apr. 19, 2011

(54) **MIXTURE OF *PROPIONIBACTERIUM JENSENII* AND *LACTOBACILLUS* SP. WITH ANTIMICROBIAL ACTIVITIES FOR THE USE AS NATURAL PRESERVATION SYSTEM**

(75) Inventors: Susanne Miescher Schwenninger, Zurich (CH); Leo Meile, Zurich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 1355 days.

(21) Appl. No.: 10/493,436

(22) PCT Filed: Oct. 30, 2002

(86) PCT No.: PCT/IB02/04521
§ 371 (c)(1),
(2), (4) Date: Oct. 6, 2004

(87) PCT Pub. No.: WO03/040349
PCT Pub. Date: May 15, 2003

(65) Prior Publication Data
US 2005/0095318 A1    May 5, 2005

(30) Foreign Application Priority Data
Nov. 6, 2001  (EP) .................................. 01125464

(51) Int. Cl.
*C12N 1/20* (2006.01)
(52) U.S. Cl. ............ 426/61; 435/42; 435/244; 435/245; 435/253.6; 435/252

(58) Field of Classification Search ................ 426/9, 52, 426/53, 54, 807, 623, 630, 636; 435/42, 435/244, 245, 253.6, 252, 252.9
See application file for complete search history.

(56) References Cited

U.S. PATENT DOCUMENTS

| 4,981,705 A |   | 1/1991 | Tomes |
| 5,096,718 A | * | 3/1992 | Ayres et al. ........................ 426/9 |
| 5,186,962 A | * | 2/1993 | Hutkins et al. ................... 426/61 |

FOREIGN PATENT DOCUMENTS
EP    0 576 780 A2    5/1995

OTHER PUBLICATIONS

Susanne Miescher, "Antimicrobial and Autolytic Systems of Dairy Propionibacteria", 1999, Swiss Federal Institute of Technology Zurich (ETHZ), Zurich, Switzerland, pp. 58-62, pp. 79-83, Diss. ETH No. 13486, XP002192334.
P. Javanainen et al., "Factors Affecting Rye Sour Dough Fermentation with Mixed-culture Pre-ferment of Lactic and Propionic Acid Bacteria", Journal of Cereal Science, vol. 18, 1993, pp. 171-185, XP-002192333.

* cited by examiner

*Primary Examiner* — Keith D Hendricks
*Assistant Examiner* — Hamid R Badr
(74) *Attorney, Agent, or Firm* — Steptoe & Johnson LLP

(57) ABSTRACT

The invention concerns a mixture of bacteria. Said mixture is a non starter culture which is free from metabolites and comprises at least one first bacterium selected from the species *Propionibacterium jensenii* and at least one second bacterium selected from the genus *Lactobacillus*. Furthermore, food, feeding stuff and medicaments comprising such a mixture, a method for manufacturing and storing such goods and the use of the mixture to inhibit fungi and bacteria are provided.

1 Claim, 3 Drawing Sheets

MIXTURE OF *PROPIONIBACTERIUM JENSENII* AND *LACTOBACILLUS* SP. WITH ANTIMICROBIAL ACTIVITIES FOR THE USE AS NATURAL PRESERVATION SYSTEM

CROSS REFERENCES TO RELATES APPLICATIONS

This application claims the priority of the European patent application No. 01 125 464.6, filed Nov. 6, 2001, the disclosure of which is incorporated herein by reference in its entirety.

TECHNICAL FIELD

The invention concerns bacteria suitable for the preservation of goods, in particular a mixture of bacteria.

BACKGROUND ART

Outgrowth of undesired micoorganisms in food products can be counteracted by different ways. Beside physical and chemical treatments, biological treatments such as fermentations by naturally resident and/or artificial ("starter") microorganisms are widely used. They can change the food conditions in which growth of undesireable organisms is less favourable or completely inhibited as is the case in wine, beer, cheese or yoghourt (Holzapfel et al. 1995; Vogel, 1996). Another system of biologically induced food preservation is the supplementation of "protective cultures" acting as "biopreservatives". Such cultures are thought
a) either to grow and competitively supress undesired organisms
b) or to grow and produce antimicrobial and antifungal agents (e.g. bacteriocins, organic acids, diacetyl, unknown metabolites)
c) or to interact by unknown mechanisms with food spoiling microorganisms.

Since protective cultures generally do not participate in specific food modification processes as starter cultures, their application can also be extended to nonfood materials.

Antimicrobial activities of propionibacteria and lactic acid bacteria make them appropriate for industrial application as biopreservatives. Bio Profit (Valio Ltd., Helsinki, Finland; Wiesby GmbH & Co., Niebüll, Germany), is a commercially available co-culture of *Lactobacillus rhamnosus* LC705 (DSM 7061) (former *Lactobacillus casei* subsp. *rhamnosus*) and *Propionibacterium freuden-reichii* subsp. *shermanii* JS (DSM 7067), that is suggested for a controlling of yeasts and moulds (Soumalainen and Mäyrä-Mäkinen, 1999) Both organisms had been cultured together and were supposed to be used as a cell containing fermentation broth inhibiting the growth of moulds and yeasts in food. Strain *Lactobacillus rhamnosus* LC705 was protected in 1993 by a European patent (EP 0 576 780) to be used as a single strain or in combination with a bacterium of the genus *Propionibacterium* or another strain of the bacterial species *Lactobacillus casei*. A second, German patent (DE 199 17 715) describes protective cultures consisting of lactic acid bacteria and inhibiting the growth of toxigenic bacteria at temperatures over 7-8° C. The cultures are suggested for a preservation of food and animal food (feeding stuff) showing only a short shelf-life below 7-8° C. As soon as the storage temperature increases, the cultures promise to inhibit the growth of spoilage bacteria. In contrast, Microgard™ (Wesman Foods, Inc., Beaverton, Oreg., USA) is a commercially available milk product fermented by a *P. freuden-reichii* ssp. *shermanii* strain, followed by a pasteurisation process. The product promises effectiveness in inhibiting selected food spoilage organisms as well as pathogenic microorganisms known to cause foodborne illnesses (Daeschel, 1989; Al-Zoreky et al., 1991). Microgard™ is approved by the US Food and Drug Administration.

DISCLOSURE OF THE INVENTION

Hence, it is a general object of the invention to provide an improved bacteria based inhibitor for the growth of fungi (yeasts, moulds) and/or bacteria as well as mixtures thereof.

Now, in order to implement this and still further objects of the invention, which will become more readily apparent as the description proceeds, the invention is manifested by the features that are mentioned in the independent claims.

It was unexpectedly found that bacteria selected from the species *Propionobacterium jensenii* and/or the genus *Lactobacillus* that are non-starter cultures and free from metabolites are suitable inhibitors of undesired microorganisms. In particular a mixture of bacteria (also referred to as inhibiting mixture or protective culture)—which is a non starter culture—and which is free from metabolites and that comprises at least one first bacterium selected from the species *Propionibacterium jensenii* and at least one second bacterium selected from the genus *Lactobacillus*, is able to inhibit at least one microorganism selected from fungi and/or bacteria as well as mixtures of fungi and bacteria which for example are responsible for the deterioration of food and feeding stuff.

This mixture of bacteria has the great advantage that—although metabolites that hitherto were thought to be responsible for protective activity are absent—the protection is as good or even better than with hitherto known cultures and undesired side effects due to metabolites (e.g. the metabolites can be toxic or also negatively influence the taste, colour of food etc.) are markedly reduced or even fully eliminated.

The mixture of bacteria is incorporated into and/or applied onto the surface of the good to be protected.

The term "metabolites" comprises all products which origin from the metabolism of the bacteria comprised by the mixture.

In this application, bacteria and fungi which are able to deteriorate food, feeding stuff, medicaments are also called "unwanted microorganisms".

The term "a mixture of bacteria free from metabolites" means that only the mixture of bacteria (e.g. separated from metabolites at least by centrifugation, preferably by centrifugation and at least one washing step), optionally together with a carrier, is incorporated into and/or applied onto the surface of the good (food, feeding stuff, medicament) to be protected from deterioration.

Furthermore, in connection with this patent application, the term "to be inhibiting, to inhibit etc." means for example that the growth or also the number or the concentration of unwanted microorganisms, for example in food and/or onto the surface of food comprising the mixture, is lower than in food and/or onto the surface of food which does not comprise such a mixture.

The term "a mixture which is a non starter culture" means a mixture that comprises bacteria which are not or not essentially adapted to the good—in particular food, feeding stuff, medicaments—to be protected by the mixture such that they do not or only minimally grow. Minimal growth means a growth of up to at most about tenfold.

A preferred mixture is a mixture of bacteria as described above that is obtainable by the process which comprises the following steps:

Firstly, an inhibiting mixture which comprises at least one first and at least one second bacterium and which mixture is free from metabolites is incorporated into a medium and/or applied onto the surface of a medium contained in a first container such that a minimum concentration as defined further below of each of said at least one first and at least one second bacteria in this medium and/or on the surface of this medium results.

The medium contained in the first and second container (the second container is described below) in or on which the inhibition of the contaminants is tested preferably is food or feeding stuff or a medicament, or much preferably solid agar medium.

The at least one first bacterium is selected from the species *Propionibacterium jensenii* and the at least one second bacterium is selected from the genus *Lactobacillus*.

As a blank, a second container is prepared comprising the same medium as said first container but no mixture of bacteria.

Then the same number of contaminants are incorporated into the medium and/or applied onto the surface of the medium contained in said first and second containers.

The term "contaminants" is equal to the term "unwanted microorganisms" and comprises fungi and/or bacteria as well as mixtures of fungi and bacteria.

The inhibiting effect of the mixture against the contaminants is determined by storing the first and second container at a suitable temperature during a suitable storage time.

In general, said suitable temperature at which this method is performed depends on the temperature at which a specific good, in particular food, feeding stuff or medicament normally is stored and/or manufactured.

The temperature at which the first and second container are usually stored is 5-26° C., preferably said temperature is at least selected from the group of approx. 6° C. and/or approx. 12° C. and/or approx. 25° C.

The term "approx." means 6±1° C., 12±1° C., 25±1° C.

The storage time at said temperature depends on the time during which the good (food, feeding stuff or a medicament) normally is stored.

The storage time usually is 7-28 days, preferably said storage time is selected at least from the group of 7 days and/or 14 days and/or 21 days and/or 28 days.

During said storage time at a specific temperature, the number or the concentration of contaminants incorporated into the medium and/or applied onto the surface of the medium contained in the first and second container is compared.

Based on this comparison (number/concentration of contaminants in said first container at a specific time versus number/concentration of contaminants in said second container at that specific time), a first and a second graph can be drawn in a coordinate system where e.g. the x-axis represents the storage time and the y-axis represents the number and/or concentration of contaminants. The first graph shows the number or concentration of the contaminants incorporated into the medium and/or applied onto the surface of the medium in the first container and the second graph shows the same measure in the medium and/or on the surface of the medium contained in the second container.

If only single strains or mixtures of strains of the same species or genus shall be investigated, the above mentioned method can be used accordingly.

The mixture is considered to be inhibiting during the stages of the storage time, if said second graph is above said first graph.

Preferably, the mixture is considered to be inhibiting if the number of contaminants in the medium and/or on the surface of the medium contained in the second container is at least about log 1 higher, preferably at least about log 2, much preferably at least about log 3, more preferably at least about log 4, even more preferably at least about log 5, most preferably at least about log 6 than the number of contaminants in the medium and/or on the surface of the medium contained in said first container during at least 3 days, preferably at least 7 days, much preferably at least 14 days, more preferably at least 21 days, most preferably 25 days.

According to a preferred embodiment of the invention, the at least one first bacterium mentioned above is *Propionibacterium jensenii* SM11.

According to another preferred embodiment of the invention, the at least one second bacterium mentioned above is selected from the group consisting of *Lactobacillus paracasei, Lactobacillus rhamnosus, Lactobacillus casei; Lactobacillus plantarum*, and mixtures thereof.

According to a further, more preferred embodiment of the invention, the at least one second bacterium is selected from one or more strains of *Lactobacillus paracasei* subsp. *paracasei*.

According to an even more preferred embodiment of the invention, the at least one second bacterium is *Lactobacillus paracasei* subsp. *paracasei* SM20 and/or *Lactobacillus paracasei* subsp. *paracasei* SM29 and/or *Lactobacillus paracasei* subsp. *paracasei* SM63, and mixtures thereof.

The ratio between the at least one first bacterium and the at least one second bacterium of the mixture—e.g. the ratio of the concentration or number of the at least one first bacterium and the concentration or number of the at least one second bacterium—preferably amounts from 1:100-100:1, preferably 1:10-10:1.

The mixtures described above provide the advantage that microorganisms selected from the group consisting of fungi, bacteria and mixtures of fungi and bacteria which are or can be pathogenic for humans and/or animals and/or which have or can have a spoilage effect—for example on food, feeding stuff, medicaments—can be inhibited.

For example in case of food—means for preservation such as chemical processes (e.g. the application of food preservatives, salting) and/or physical processes (e.g. heat, UV-rays, Gamma-rays, x-rays), packaging using protective gases (e.g. $N_2$, $CO_2$) or vacuum packaging can be reduced or totally omitted without reduction of the storage time/shelf life of the food.

As a consequence thereof, especially low processed food or also low processed ingredients which for example are added to high processed food can be stored during a longer period without biological deterioration or also can be better exported to other countries.

If desired, the mixture can also be used in connection with the preservation processes mentioned above.

Using such preservation processes in combination with the mixture, it is a prerequisite that the mixture still can perform its protective purpose.

This means for example that after the application of said preservation process, the good to be protected still has to comprise at least the following minimum concentrations of viable cells (cfu=colony forming unit).

The minimum concentration of the at least one first or the at least one second bacterium in the food in view of protection amounts at least to about $1 \times 10^7$ cfu/ml, preferably at least to about $1 \times 10^8$ cfu/ml, even more preferably at least to about $1 \times 10^9$ cfu/ml or at least to about $1 \times 10^7$ cfu/g, preferably at least to about $1 \times 10^8$ cfu/g, even more preferably at least to about $1\times10^9$ cfu/g and/or on the surface of the food at least to about $1\times10^6$ cfu/cm$^2$, preferably at least to about $1\times10^7$ cfu/cm$^2$, much preferably at least to about $1\times10^8$ cfu/cm$^2$, even more preferably at least to about $1\times10^9$ cfu/cm$^2$.

If higher activity against contaminants is desired, concentrations of at least about $1\times10^{10}$ cfu/ml or at least about $1\times10^{10}$ cfu/g and/or at least about $1\times10^{10}$ cfu/cm$^2$ are possible.

The minimum concentrations mentioned above go out from the experimental observation that the higher the concentration or number of the protective culture is, the more the fungi and/or bacteria as well as mixtures thereof are inhibited.

While some protection is already observed if the first and second bacteria are present in amounts of $1\times10^7$ cfu/ml or cfu/g, the protection is much better if the at least-one first bacterium and the at least one second bacterium combined with each other to the mixture of bacteria amount at least to about $5\times10^7$ cfu/ml or at least to about $5\times10^7$ cfu/g and/or at least to about $5\times10^6$ cfu/cm$^2$ for the at least one first bacterium and at least to about $1\times10^8$ cfu/ml or at least to about $1\times10^8$ cfu/g and/or at least to about $1\times10^7$ cfu/cm$^2$ for the at least one second bacterium. Very satisfying results were achieved with at least about $1\times10^8$ cfu/ml or at least about $1\times10^8$ cfu/g and/or at least about $1\times10^7$ cm$^2$ for the at least one first bacterium and at least about $1\times10^8$ cfu/ml or at least about $1\times10^8$ cfu/g and/or at least about $1\times10^7$ cm$^2$ for the at least one second bacterium. Presently preferred are at least about $5\times10^8$ cfu/ml or at least about $5\times10^8$ cfu/g and/or at least about $5\times10^7$ cfu/cm$^2$ for the at least one first bacterium and at least to about $5\times10^8$ cfu/ml or at least about $5\times10^8$ cfu/g and/or at least about $5\times10^7$ cfu/cm$^2$ for the at least one second bacterium.

The minimum concentrations and preferred concentrations mentioned above apply also to medicaments and feeding stuff.

The determination of the surface concentration can be performed by two methods:

(i) by measuring the applied amount, e.g. in spraying application, or preferably (ii) by measuring the concentration of a specific volume with well defined application surface and comprising the whole diffusion zone of the mixture of bacteria.

The term "at least one first bacterium of $1\times10^7$ cfu/ml" means that a first bacterium and optionally one or more other first bacteria which are different from each other and which all belong to the genus *Propionibacterium jensenii* are simultaneously present, whereby all said first bacteria together form a concentration of $1\times10^7$ cfu/ml. This definition also applies to equivalent passages in the application.

The minimum concentrations defined above have to be given in any stage after the completion of the manufacturing process of the food, feeding stuff or medicament.

In any case, the concentration of the mixture must be higher than or at least equal to the minimum concentration before the beginning of the storage.

Preferably, food, feeding stuff or medicaments comprise such a concentration of the bacteria of the mixture that the concentration of the bacteria and/or fungi or mixture of bacteria and fungi is kept below the requirements mentioned in the food regulation of the respective country where this invention is used.

Preferably, but not necessarily, these minimum concentrations also apply during the performance of the manufacturing method.

If the concentration of the bacteria of the mixture in the good and/or onto the surface of the good to be protected falls below the minimum concentration during the performance of the manufacturing method because of for example the application of preservation processes which reduce the viable cells (heat, UV-rays etc.) or as a consequence of concentration changes during the manufacturing (e.g. by addition of further ingredients etc.) cells can be added during the performance of the manufacturing. In case of a manufacturing method comprising a long lasting step, it is important that the minimum concentration is already present during said step such as for example during the ripening of sausages.

If a reduction of the concentration of viable cells takes place during the storage such that the required minimum concentration is not given any more, additional viable cells have to be added if possible.

In general, the concentration of the mixture of bacteria in food, feeding stuff and medicaments can be higher than the minimum concentrations mentioned above. But the concentrations have to be selected such that the food, feeding stuff or the medicament is not affected by undesired deteriorations. This means for example that the mixture does not influence the sensory or other quality properties of the food (e.g. discoloration etc.).

Besides the mixtures described above, the invention also provides a method for manufacturing e.g. feeding stuff, medicaments, and preferably food, comprising such mixtures.

This manufacturing method allows that unwanted microorganisms are not able to grow.

In the following, this method is described by means of food, but this does not exclude that the following teaching can also be applied to the manufacturing of other goods, e.g. feeding stuff and medicaments.

The method comprises the following steps: Firstly, the mixture is added during the manufacturing of the food in an amount such that the concentration of the at least one first bacterium and the at least one second bacterium in the food each amounts at least to the minimum concentration cfu/ml or cfu/g of the food and/or at least to the minimum concentration cfu/cm$^2$ of the surface of the food.

In general, the mixture has to be added at a stage of the manufacturing method or prior to the storage such that it can be evenly distributed in the good and/or onto the surface of the good to be protected.

The mixture preferably is applied at a stage prior to a significant contamination with unwanted microorganisms.

In a second step of the manufacturing, e.g. after the addition of the mixture, one or more parameters of the manufacturing method have to be controlled such that the concentration of the mixture decreases or, preferably remains constant. While decrease in concentration can be "healed" as described above, significant growth must be avoided.

Such parameters are for example the temperature, pressure or also the ingredients of the food etc.

By the term "constant" it is intended—once the mixture is added to the good, e.g. food or feeding stuff or medicament—that the concentration of the mixture remains constant. Such constant mixture preferably is added in an amount such that at least the minimum concentration as defined in this application results. By the term "constant", is also intended an increase of number or concentration of the bacteria of the mixture by means of growth of the bacteria up to at most tenfold.

In case the manufacturing method comprises one or more fermentation steps, the mixture—if added prior to the fermentation—must not have a negative influence on the microorganisms (e.g. bacteria, moulds, yeasts or mixtures thereof) responsible for said one or more fermentations (e.g. reduction of the fermentation activity).

If the mixture has such a negative influence on these microorganisms, the mixture is added after said one or more critical fermentation steps or after the completion of the manufacturing method.

Also in manufacturing methods comprising steps that might be affected by the mixture of bacteria, said bacteria are added after such one or more steps.

Furthermore, the invention provides a method for storing goods, in particular feeding stuff, medicaments and preferably food wherein the growth of unwanted microorganisms during storage is inhibited.

This method for storage can be used for the storage of e.g. food, feeding stuff or medicaments which are manufactured according to the manufacturing method of the invention or by known manufacturing methods.

Only during the manufacturing method according to the invention, the parameter or parameters of the manufacturing method are controlled such that the concentration of the mixture remains constant.

Using other e.g. common manufacturing methods, there is no or only partial such control. Therefore, the mixture should be added in such manufacturing method at a stage after which the concentration of the mixture remains constant.

The method for storing comprises the step of controlling the storage parameter or storage parameters during the storage such that the concentration of the at least one first and at least one second bacterium remains constant.

Possible storage parameters are for example the temperature, storage atmosphere around the good, storage atmosphere within the packaging of the good etc.

The term "storage" means the time after completion of the manufacturing of the good, e.g. food, feeding stuff or medicament and therefore said term for example can also comprise transportation.

The mixture of bacteria according to the invention preferably is contained in and/or applied onto the surface of food, feeding stuff or medicaments.

Such food preferably are dairy products, more preferably sour milk products.

Furthermore, meat and meat products are also preferred.

Dairy products are for example raw milk, heat-treated or microfiltrated milk, butter, curdled milk, sour cream, skim milk, cream, yoghurt, buttermilk, curd, cheese, kefir, kumiss, puddings, sour milk, acidophilus sourmilk, langfil (ropy milk), bifidus sourmilk, junket, sour cream butter.

Meat is for example portioned fresh beef or poultry meat or minced meat.

Meat products preferably are ready to eat sausages, pet food, nitrite and nitrate cured meat (pickled raw meat), cooked salt meat, raw sausage etc.

Products like for example delicatessen salads made of meat, fish, molluscs, crustaceans, vegetable, pasta and mixtures thereof, but also fish, fish products, molluscs, crustaceans, fruits, fruit products, nuts, nut products, and vegetables such as potatoes, vegetable products, corn, corn products can be protected by the mixture.

Possible combinations of the food mentioned above comprising the mixture according to the invention are also felt to fall under the present invention.

Feeding stuff preferably are products derived from nuts, corn, gras.

Medicaments which can be protected by the mixture are natural and organic remedies.

According to one embodiment of the invention, food, feeding stuff or medicaments are treated with a powder comprising the mixture which powder optionally comprises suitable carrier substances. Suitable carrier substances are for example saccharides, preferably monosaccharides, disaccharides or their derivatives.

According to a further preferred embodiment of the invention, food, feeding stuff or medicaments are treated with a liquid medium comprising the mixture. Such a liquid medium must be designed such that it guarantees the survival of the mixture. It can be for example an aqueous medium such as a liquid milk product or a physiological sodium chloride solution.

According to a preferred embodiment of the invention, the mixture is incorporated into the food, feeding stuff or medicament by mixing, spraying etc., whereby by spraying or another suitable type of application such as dipping, the mixture is applied onto the surface of food, feeding stuff or medicament.

In case of dairy products, the mixture preferably is comprised in a liquid, whereby the liquid is added to the good to be protected. The mixture can also be added as a deep freezed or freeze-dried concentrate.

The mixture according to the invention that is preferably incorporated into and/or applied on the surface of food, feeding stuff or medicaments, more preferably into and/or on those specified above, allows in particular the inhibition of bacteria such as *Listeria innocua, Listeria monocytogenes, Salmonella typhimurium, Staphylococcus aureaus, Escherichia coli, Serratia liquefaciens, Citrobacter freundii, Klebsiella pneumoniae, Enterobacter cloacae, Enterococcus faecalis, Bacillus subtilis, Bacillus cereus, Bacillus anthracis* and mixtures of these bacteria, lower eukaryotes such as algae and mixtures of lower eukaryotes, fungi such as *Candida magnoliae, Candida parapsilosis, Candida silvicola, Candida valida, Candida pulcherrima, Candida reukaufii, Candida krusei, Candida* sp.*, Sporobolomyces salmonicolor, Zygosaccharomyces bailii, Penicillium* sp., mixtures of these fungi as well as mixtures of the bacteria and fungi mentioned above as well as mixtures of the bacteria and fungi and lower eukaryotes mentioned above.

The invention is not considered to be limited to the bacteria, fungi, food, feeding stuff and medicaments explicitly mentioned in this application.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

EXAMPLES

Figure 1:
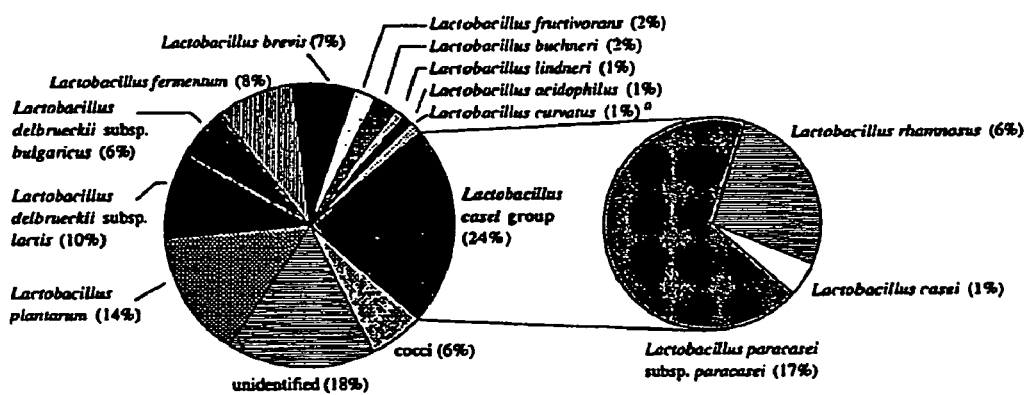
FIG. 1 shows a composition of 82 isolates on MRS agar originating from raw milk, cheese, yoghurt, black olives, salami as well as mais and gras silage showing antifungal activities in an agar spot assay and being identified with API 50 CHL. [a] identified as *Lactobacillus paracasei* subsp. *paracasei* analysing the 16S rRNA gene.

Material and Methods
Bacterial Strains and Media
Bacterial strains and fungi used in this study are listed in Table 1.

TABLE 1

Microbial strains used in this study.

| Strain | Relevant characteristics | Temp (° C.) | Medium | Reference |
|---|---|---|---|---|
| Propionibacteria and lactobacilli | | | | |
| *Propionibacterium jensenii* | | | | |
| SM11 | Antimicrobial activity | 32 | NLB | LME[a] |
| *Lactobacillus casei* | | | | |
| DSM 20011[τ] | Type strain | 30 | MRS | DSM[b] |
| *Lactobacillus paracasei* subsp. *paracasei* | | | | |
| SM20 | Antimicrobial activity | 32 | MRS | This study |
| SM29 | Antimicrobial activity | 32 | MRS | This study |
| SM63 | Antimicrobial activity | 32 | MRS | This study |
| DSM 5622[τ] | Type strain | 30 | MRS | DSM |
| *Lactobacillus plantarum* | | | | |
| SM17 | Antimicrobial activity | 32 | MRS | This study |
| SM39 | Antimicrobial activity | 32 | MRS | This study |
| *Lactobacillus rhamnosus* | | | | |
| DSM 20021[τ] | Type strain | 37 | MRS | DSM |
| Other strains | | | | |
| *Bacillus cereus* | | | | |
| DSM 31[τ] | Type strain | 30 | BHI | DSM |
| *Bacillus subtilis* | | | | |
| 168 | | 30 | BHI | LME |
| *Enterococcus faecalis* | | | | |
| DS5 | | 37 | BHI | LME |
| *Staphylococcus aureaus* | | | | |
| VF4 | | 37 | BHI | LME |
| *Listeria innocua* | | | | |
| L17 | | 37 | BHI | LME |
| *Listeria monocytogenes* | | | | |
| M1 | | 37 | BHI | LME |

TABLE 1-continued

Microbial strains used in this study.

| Strain | Relevant characteristics | Temp (° C.) | Medium | Reference |
|---|---|---|---|---|
| *Citrobacter freundii* | | | | |
| SG84 | | 30 | BHI | LME |
| *Enterobacter cloacae* | | | | |
| SG95 | | 30 | BHI | LME |
| *Escherichia coli* | | | | |
| B | | 37 | BHI | LME |
| SG63 | | 37 | BHI | LME |
| *Klebsiella pneumoniae* | | | | |
| SG89 | | 30 | BHI | LME |
| *Salmonella typhimurium* | | | | |
| ATCC 14028 | | 37 | BHI | ATCC[c] |
| *Serratia liquefaciens* | | | | |
| SG64 | | 30 | BHI | LME |
| *Candida* sp. | | | | |
| 1-50/15 | | 25 | YM | Miescher (1999) |
| *Candida krusei* | | | | |
| 3-69/2 | | 25 | YM | Miescher (1999) |
| *Candida magnoliae* | | | | |
| 1-35/1 | | 25 | YM | Miescher (1999) |
| *Candida parapsilosis* | | | | |
| 4-5/1 | | 25 | YM | Miescher (1999) |
| *Candida pulcherrima* | | | | |
| 1-50/13 | | 25 | YM | Miescher (1999) |
| *Candida reukaufii* | | | | |
| 4-73/4 | | 25 | YM | Miescher (1999) |
| *Candida silvicola* | | | | |
| 4-42/1 | | 25 | YM | Miescher (1999) |
| *Candida valida* | | | | |
| 1-48/8 | | 25 | YM | Miescher (1999) |
| *Sporobolomyces salmonicolor* | | | | |
| 3-46/2 | | 25 | YM | Miescher (1999) |
| *Zygosaccharomyces bailii* | | | | |
| 1-48/1 | | 25 | YM | Miescher (1999) |
| *Penicillium sp.* | | | | |
| 2-21/7 | | 25 | YM | Miescher (1999) |
| 2-21/12 | | 25 | YM | Miescher (1999) |
| 2-52/2 | | 25 | YM | Miescher (1999) |
| 3-58/3 | | 25 | YM | Miescher (1999) |

[a]Laboratory for Food Microbiology, Zurich, Switzerland
[b]German Collection of Microorganisms and Cell Cultures, Braunschweig, Germany
[c]American Type Culture Collection, Manassas, VA, USA
[T]Type strain

*Propionibacterium* strains were grown in NLB broth that consisted of 1% trypticase soy broth without dextrose (BBL Microbiology Systems, Cockeysville, Md., USA), 1% yeast extract and 1% sodium lactate syrup (Sigma Chemical Co., St. Louis, Mo., USA) as described by Grinstead and Barefoot (1992). *Lactobacilli* were propagated in MRS broth with 0.1% Tween 80 (Biolife, Italy). All other strains were grown in BHI broth (Biolife, Italy) at growth conditions given in Table 1. Bacterial cultures were maintained as frozen stocks at −80° C. in broth containing 30% glycerol. Yeasts and moulds were cultured in YM medium (Difco, Detroit, Mich., USA) and maintained at 4° C. on solid agar medium.

Commercial starters for yoghurt fermentation were obtained from Danisco Cultor Niebüll GmbH, Germany, consisting of different strains of *Lactobacillus bulgaricus* and *Streptococcus thermophilus*.

Protective cultures were produced by growing the strains separately in supplemented whey permeate (SWP1) that consisted of 5.5% whey permeate (mmi, Switzerland), 1% yeast extract (Becton Dickinson, Md., USA) and 2% casein hydrolysate (Merck, Germany) for 72 h at 32° C. The cells were harvested by centrifugation, washed once or twice in 0.85% NaCl and resuspended in tyndallized skim milk (Difco, Detroit, Mich., USA) or in 0.85% NaCl in a necessary concentration ranging from 10- to 100-fold. Tyndallized skim milk was previously heat treated three times at 90° C. for 30 min on three following days.

A scale up and a process optimisation was performed by growing the cells separately in a 8-1 or a 19-1 bioreactor (type L1523; Bioengineering, Switzerland). at 32° C., with an agitation of 250 rpm using 2% inoculum. Fermentation was performed in supplemented whey permeate (SWP2) that consisted of 5.5% whey permeate, 1% yeast extract and 2% glucose. The pH was controlled at 6.0 adding 3 M NaOH. Simultaneously with the pH control, a feed of nutrients was achieved with 20% yeast extract and 20% glucose. The inoculum was grown in supplemented whey permeate (SWP1) at 32° C. for 72 h without agitation. Samples were withdrawn from the fermentations periodically and analysed for cell concentrations and optical density at 650 nm. Lactobacilli were grown for 72 h, propionibacteria for 90 h. The cells were harvested, washed and concentrated as described above.

Isolation of Lactic Acid Bacteria 10 g of food sample was stomached for 2 minutes with 90 ml of dilution-buffer (0.85% NaCl, 0.1% peptone), serially diluted and plated on MRS agar with 0.1% Tween 80. Milk samples were directly diluted and plated. The plates were incubated under anaerobic conditions at 37° C. for 3 days. From each food sample, a variety of different colonies was chosen for a screening for antimicrobial activities.

Screening Methods for Antimicrobial Activities

Two methods were used:

(1) Agar spot assay: The producer culture was spot inoculated onto an agar plate according to Grinstead and Barefoot (1992) and incubated at optimal growth conditions (Table 1). Each plate was overlaid with 6 ml of tempered soft agar (0.6%) containing 0.2 ml of an indicator culture which had grown up to a density of 0.2. The optical density of bacteria was measured at 650 nm, that of yeasts and moulds at 580 nm. Agar medium, soft agar medium and incubation of plates was chosen appropriate to the test and indicator organisms. Inhibition of the indicator lawn was monitored after 24 to 48 h for bacteria, fungi were daily scored for inhibition, after 3 days at 25° C.

(2) Well diffusion test: Wells of a diameter of 7 mm were cut to agar plates and filled with cell-free supernatants of bacterial cultures as described by Daeschel (1992). After complete diffusion of the liquid, soft agar containing an indicator organism was poured over the plates to demonstrate inhibitory activity as described above. Agar medium, soft agar medium and incubation of plates was chosen appropriate to the test and indicator organisms.

Characterisation and Identification of Bacterial Isolates

Isolates grown on MRS agar showing antimicrobial activities were Gram-stained and examined microscopically for cellular morphology. Furthermore catalase activity was tested by spotting colonies with 30% hydrogen peroxide and a staining of spores was done. A preliminary strain identification was done using API 50 CHL (bioMérieux SA, Marcy l'Etoile, France). Additionally, proteolysis was determined in MRS agar with 5% and 10 % skim milk and production of organic acids was analysed enzymatically (Boehringer Mannheim, Germany; kit used for D/L-lactic acid: E1 112 821/kit used for acetic acid: E0 148 261). Furthermore, growth conditions were determined in MRS broth at different temperatures for 72 h and with salinities of 5% and 10% at 32° C. for 72 h.

Identification of selected strains by partial 16S rDNA sequencing

Amplification of 16S rDNA was carried out using directly a colony of the corresponding strain. PCR was performed with universal oligonucleotides bak4 (Goldenberger, 1997) and bak11w (Greisen et al., 1994 modified by Dasen et al. 1998) using 40 cycles. Annealing was achieved at 56° C. for 30sec and extension occurred with Taq DNA polymerase (Amersham Pharmacia Biotech, Uppsala, Sweden) at 72° C. for 2 min, DNA strand separation was performed at 95° C. for 5 sec. Amplified DNA was purified using the GFX'M PCR DNA and Gel Band Purification Kit (Amersham Pharmacia Biotech, Uppsala, Sweden). Automated cycle sequencing was done with the Terminator Ready Reaction Mix (Amersham Pharmacia Biotech, Uppsala, Sweden) and oligonucleotides targeting the 16S rDNA (SEQ ID NOS 1-11, respectively, in order of appearance)(Table 2).

TABLE 2

Oligonucleotides targeting the 16S rDNA.

| Name | Sequence | Comment | Reference |
| --- | --- | --- | --- |
| Y2 | 5'-TGGTCAQACGAACGCTAGGCCCC-3' | Conserved 16S rDNA[a] | Young et al. (1991) |
| casei | 5'-TGCACTGAGATTCGACTTAA-3' | *Lactobaciilus casci* 16S rDNA | Ward and Timmins (1999) |
| para | 5'-CACCGAGATTCAACATGG-3' | *Lactobacillus paracasei* subsp. *paracasei* 16S rDNA | Ward and Timmins (1999) |
| rham | 5'-TGCATCTTGATTTAATTTTG-3' | *Lactobacillus rhamnosus* 16S rDNA | Ward and Timmins (1999) |
| bak4 | 5'-AGGAGGTGATCCARCCGCA-3' | Conserved 16S rDNA | Greisen et al. (1994) |
| bak11w | 5'-AGTTTGATCMTGGCTCAG-3' | Conserved 16S rDNA | Goldenberger (1997) |
| eub338 | 5'-ACTCCTACGGGAGGCAGC-3' | Conserved 16S rDNA | Amann et al. (1995) |
| uni515 | 5'-ACCGCGGCTGCTGGCAC-3' | Conserved 16S rDNA | Lane (1991) |
| uni785 | 5'-GGMTTAGATACCCTGGTAGTCC-3' | Conserved 16S rDNA | Amann et al. (1995) |
| uni1088 | 5'-CGTTAAGTCCCGCAACCGAGC-3' | Conserved 16S rDNA | Amann et al. (1995) |
| uni1392 | 5'-GTACACACCGCCCGTCA-3' | Conserved 16S rDNA | Lane (1991) |

[a]corresponding to a conserved region of most of the known bacterial 16S rDNA sequences 35 cycles were performed as follows: 96° C. for 10 sec, 50° C. for 30 sec, 60° C. for 4 min. Nucleotide sequencing of both strands from cloned DNA was performed by the dideoxy chain termination method (Sanger et al., 1977) with primer walking using the BigDye Terminator Cycle Sequencing Ready Reaction Kit and the ABI PRISM ABI 310 Genetic Analyser apparatus (Applied Biosystems, Foster City, Calif., USA) for analysis. DNA sequence analysis, sequence alignments, and sequence database searching were conducted with programs contained within the Sequence Analysis Software Package (version 10.0) licensed from the Genetics Computer Group (University of Wisconsin, Madison, Wis., USA).

Sequences were compared by the algorithm of Pearson and Lipman (1988) (FastA and TFastA) with sequences in the GenEMBL database copy.

Differentiation of *Lactobacillus casei*, *Lactobacillus racasei* and *Lactobacillus rhamnosus* by Polymerase Chain Reaction Amplification of 16S rDNA was carried out as described by Ward and Timmins (1999) with some modifications. A 290-bp fragment of the 16S rDNA was amplified using species-specific primers (casei, para, rham) in conjunction with primer Y2 corresponding to a conserved region of the 16S rDNA (Table 2). Each 50-µl reaction contained 2.5 U of Taq polymerase, 10 mM Tris-HCl (pH 9.0), 1.5 mM $MgCl_2$, 50 mM KCl, 1 mM dNTP Set, 1 µM each primer and one colony of the corresponding strain. Taq polymerase, buffers and dNTP Set for PCR were obtained from Amersham Pharmacia Biotech (Uppsala, Sweden). Oligonucleotides were synthesised by Microsynth (Balgach, Switzerland). The temperature program was as described by Young et al. (1991): 300 s at 93° C., 35 cycles of (45 s at 93° C., 45 s at 62° C. and 120 s at 72° C.) and 300 s at 72° C. with a final cooling to 4° C. Amplification products were separated on a 2% agarose gel.

Investigation of Antimicrobial Activities in Agar Plates

Agar plates were prepared, supplemented with *Propionibacterium jensenii* SM11 or an antimicrobial *Lactobacillus* or a combination of both. The cultures were previously grown separately for 72 h at 32° C. in supplemented whey permeate (SWP1), centrifugated, washed once and resuspended (1:1) in 0.85% NaCl and then serially diluted in dilution-buffer (0.85% NaCl, 0.1% peptone). Portions of 20 ml of agar were prepared with 10% of each dilution to give a final level of $10^5$, $10^6$, $10^7$ and $10^8$ cfu/ml. Agar plates were poured and after solidifying, portions of approximately 2-5 µl of broth cultures of the indicator strains were spot inoculated on the plates. YM agar was used for yeasts and moulds and BHI agar for bacteria. Triplex of the agar plates were stored at 6° C., 12° C. and 25° C. for up to 4 weeks and the growth of indicator organisms was controlled weekly for 6° C. or daily for 12° C. and 25° C. As a control, agar plates without supplementation of lactobacilli and propionibacteria were prepared as well as agar plates with an addition of 1 g/l Ka-Sorbat (EU-Richtlinie, Nr. 95/2/HG).

Investigation of Antifungal Activities in a Food Model

A food model was set up with portions of 50 g tyndallized skim milk (Difco, Detroit, Mich., USA) that were fermented with a commercial yoghurt culture. Test samples were additionally inoculated with a protective culture (1% of a 100-fold concentrated culture of *Propionibacterium jensenii* SM11 and 1% of a 100-fold concentrated culture of an antifungal *Lactobacillus*) to give a level of $10^8$ cells/g of each. The cultures were previously washed twice and resuspended in tyndallized skim milk. To get comparable results, the control sample was mixed with 2% tyndallized skim milk. The fermentation was done for about 5 hours at 42° C. until the pH reached 4.6. All samples were contaminated with *Candida pulcherrima* 1-50/13 at a final level of $10^2$ cfu/g. Additionally a control sample was prepared without a yeasts contamination. Samples were stored at 6° C. for 7 weeks and protective propionibacteria and lactobacilli as well as yeasts were enumerated weekly. Simultaneously, pH was controlled weekly.

Inhibition of Fungi in Yoghurt by Protective Cultures

Portions of 200 g milk enriched with 5$ cream (35% fat, 2.5% proteins), 2% skim milk powder and 5% sugar were heat treated at 90° C. for 10 min and then fermented with a commercial yoghurt culture. Test samples were additionally inoculated with a protective culture (0.1% or 1% of a 100-fold concentrated culture of *Propionibacterium jensenii* SM11 and 0.1% or 1% of a 100-fold concentrated culture of an antifungal *Lactobacillus*-strain) to give a level of $10^7$ or $10^8$ cfu/g of each. Protective cultures were previously washed twice and resuspended in tyndallized skim milk. The fermentation was done for about 5 hours at 42° C. until the pH reached 4.6. The yoghurt was contaminated with a mix of *Candida pulcherrima* 1-50/13, *Candida magnoliae* 1-35/1, *Candida parapsilosis* 4-5/1 and *Zygosaccharomyces bailii* 1-48/1 at a final level of $10^2$ cfu/g. Additionally a control sample was prepared without a yeasts contamination. The yoghurt was stored at 6° C. for 4 weeks and yeasts were enumerated weekly. Simultaneously, pH was controlled weekly. At day 1 and after 3 weeks of storage, protective propionibacteria and lactobacilli were enumerated and furthermore after 3 weeks lactate and acetate were determined enzymatically (Boehringer Mannheim, Germany; kit used for D/L-lactic acid: E1 112 821/kit used for acetic acid: E0 148 261).

Scale Up of the Application of a Protective Culture in Yoghurt

Scale up trials with yoghurt comprising the protective culture were also performed as described above.

Inhibition of Yeasts on a Cheese Surface by Protective Cultures

Equal cubes (2.5×4.8×8 cm) of 100 g hard cheese (Gruyère) were prepared. To avoid a contamination, with microorganisms of the cheese surface, 3-5 mm of the cheese's rind were previously cut off. One batch of cheese was soaked with each cube's side in a protective culture (5 ml of a 20-fold concentrated culture of *Propionibacterium jensenii* SM11 and 5ml of a 20-fold concentrated culture of an antifungal *Lactobacillus*-strain) to give a level of $10^8$ cfu/g cheese surface of each. Protective cultures were previously washed twice and resuspended in 0.85% NaCl. Two other batches of cheese were prepared with 10-fold and 100-fold diluted protective cultures. Onto the surface of the cubes of all three batches, about 3 ml of the respective concentrated protective culture was thus applied. Then, the cheeses were contaminated with 1 ml ($10^4$ cfu/ml) of a mix of *Candida pulcherrima* 1-50/13, *Candida magnoliae* 1-35/1, *Candida parapsilosis* 4-5/1 and *Zygosaccharomyces bailii* 1-48/1 to reach a final level of $10^2$ cfu/g cheese surface. The surface of the cheeses was defined as a layer of about 3 mm from the outside of the cube. A control sample was prepared without an addition of yeasts. The cheeses were sealed in sterile plastic bags and stored for 3 weeks at 6° C. At day 1 and after 3 weeks of storage, the level of protective propionibacteria and lactobacilli was determined as well as the number of yeasts.

Inhibition of *Listeria* by a Protective Culture in a Food Model

Two food models were set up to test antibacterial activities of a protective culture against *Listeria*.

(1) Inhibition of *Listeria innocua* L17 and *Listeria monocytogenes* M1 by a Protective Culture in Cream:

200 g of pasteurised half-cream (25% fat, 2.5% proteins) were inoculated with *Listeria innocua* L17 or *Listeria monocytogenes* M1, respectively, at a final level of $10^3$ cfu/g and were then divided into two portions of 100 g in sterile flasks. One sample was inoculated with a protective culture (5% of a 20-fold concentrated culture of *Propionibacterium jensenii* SM11 and 5% of a 20-fold concentrated culture of *Lactobacillus paracasei* subsp. *paracasei* SM20) to give a level of $10^8$ cfu/g of each. Protective cultures were previously-washed twice and resuspended in tyndallized skim milk. To get comparable concentrations, 10% of tyndallized skim milk were added to the control sample. All samples were stored at 6° C. for 4 weeks. The pH and growth of *Listeria* was controlled weekly, after 1 day, and after 4 weeks the level of protective culture was checked as well. A second batch was prepared as described and stored at 25° C. for 3 weeks. Similarly, the numbers of protective cultures and of *Listeria* were determined at the beginning and at the end of storage.

(2) Inhibition of *Listeria innocua* L17 by protective cultures in minced meat: Portions of 100 g of minced meat were mixed with a protective culture (5% of a 20-fold concentrated culture of *Propionibacterium jensenii* SM11 and 5% of a 20-fold concentrated culture of an antimicrobial *Lactobacillus*-strain) to give a level of $10^8$ cfu/g of each. Protective cultures were previously washed twice and resuspended in 0.85% NaCl. The meat was contaminated with *Listeria innocua* L17 at a final concentration of $10^3$ cfu/g and was then stored at 6° C. for 8 weeks. Additionally a control sample was prepared without protective culture. To get comparable concentrations, 10% of 0.85% NaCl were added to this sample. Protective propionibacteria and lactobacilli as well as *Listeria innocua* L17 were enumerated weekly, pH was controlled at the end of the storage period.

Results

Antifungal Activities in *Lactobacillus* sp.

A preliminary screening for antimicrobial activities was performed with 1424 isolates on MRS agar originating from raw milk, cheese, yoghurt, black olives, sour dough, salami, as well as maize and gras silage. A total of 82 strains showed activities in an agar spot assay against the fungi listed in Table 1. These isolates were further characterised by Gram-staining, catalase-activity, micoscropy and forming of spores. As depicted in FIG. 1 the species belonging to the *Lactobacillus casei*-group showed predominantly antifungal activities with a share of 24%. A preliminary identification with API 50 CHL classified these isolates as *Lactobacillus casei*, *Lactobacillus paracasei* subsp. *paracasei* and *Lactobacillus rhamnosus*. Furthermore the species *Lactobacillus plantarum* showed high inhibitory activities towards the tested fungi. A total of 6% of the antifungal isolates appeared to be cocci and 18% remained unidentified using fermentation patterns.

Identification and Characterisation of Three High Antifungal lactobacilli

Three isolates with high antifungal activities were further identified using sequencing analysis of the 16S rDNA. Studying carbohydrate metabolisms, they were previously identified as *Lactobacillus paracasei* subsp. *paracasei* (SM20 and SM29) and *Lactobacillus curvatus* (SM63). Sequencing analysis of the 16S rDNA of these strains revealed the species *Lactobacillus paracasei* subsp. *paracasei* for strain SM20 with an identity of 100% in 1519 nucleotides overlapping with the partial sequence of the 16S rDNA of *Lactobacillus paracasei* JCM8130 (D79212) and with the partial 16S rDNA-sequence of a *Lactobacillus casei* (D86517). A total of 1520 nucleotides were identified from the 16S rDNA of strain SM20. 1528 nucleotides sequenced from strain SM29 showed an identity of 99.9% in 1520 nucleotides overlapping with the partial sequence of the 16S rRNA gene of a *Lactobacillus casei* (D86517) and with the partial 16S rDNA-sequence of *Lactobacillus paracasei* JCM8130 (D79212). Surprisingly, 1515 nucleotides identified of the 16S rRNA gene of strain SM63 showed also an identity of 99.9% in 1493 nucleotides overlapping with the 16S rRNA gene of a *Lactobacillus casei* (D86517) and with the partial sequence of the 16S rDNA of *Lactobacillus paracasei* JCM8130 (D79212).

Figure 2:
FIG. 2 shows a 2% agarose gel of the amplification of a 290-bp product obtained using the casei-group-specific oligonucleotides in conjunction with primer Y2 (Table 2). (A) *Lactobacillus paracasei* subsp. *paracasei* SM20; (B) *Lactobacillus paracasei* subsp. *paracasei* SM29; (C) *Lactobacillus paracasei* subsp. *paracasei* SM63; (D) *Lactobacillus casei* DSM 20011$^T$; (E) *Lactobacillus paracasei* subsp. *paracasei* DSM 5622$^T$ and (F) *Lactobacillus rhamnosus* DSM 20021$^T$; 1, 4, 7, 10, 13, 16, *casei*/Y2; 2, 5, 8, 11, 14, 17, para/Y2; 3, 6, 9, 12, 15, 18, rham/Y2; 19, negative control; kb, linear DNA kb-ladder; pUC, pUC19-DNA/MspI(HpaII) marker.

Since members of the casei-group form a very homologous group concerning phenotypic criteria as well as sequence data of the 16S rRNA gene, Ward and Timmins (1999) developed a simple PCR approach to differentiate the species *Lactobacillus casei*, *Lactobacillus paracasei* and *Lactobacillus rhamnosus* based on the reclassification by Collins et al. (1989). FIG. 2 shows a specific product of 290 bp for strains SM20, SM29 and SM63 amplified in a polymerase chain reaction with the *Lactobacillus paracasei*-specific primer used in conjunction with primer Y2, both targeting the 16S rRNA gene. The type strains of *Lactobacillus casei* (DSM 20011$^T$) and *Lactobacillus paracasei* subsp. *paracasei* (DSM 5622$^T$) also revealed a 290-bp band with the corresponding primers. Surprisingly, *Lactobacillus rhamnosus* (DSM 20021$^T$) did not show the specific band after polymerase chain reaction with Y2 and rham. Furthermore, no products were observed if this primer pair (Y2/rham) was used with the strains to be identified. Thus, the isolates SM20, SM29 and SM63 were identified as *Lactobacillus paracasei* subsp. *paracasei*. Table 3 shows a summary of the identification of the three isolates as well as their characterisation.

TABLE 3

Identification and characterisation of strains SM20, SM29, SM63 and SM11.

| Strain | Origin | Micoscropy | Spores | Acid produced from$^a$ | Fermentation products$^b$ | Growth conditions |
|---|---|---|---|---|---|---|
| SM20 | Raw milk | short rods in chains, Gram-positive$^e$ | negative | Ribose, Galactose, D-Glucose, D-Fructose, D-Mannose, Mannitol, Sorbitol, N Acetyl glucosamine, Amygdaline, Arbutine, Escuilne, Salicine, Cellobiose, Maltose, Lactose, Saccharose, Trehalose, Inuline, Melezitose, | D-, L-Lactate | 15–45° C. (Opt.: 32–37° C. |

TABLE 3-continued

Identification and characterisation of strains SM20, SM29, SM63 and SM11.

| Strain | Source | Morphology | | Sugars (API 50 CHL) | Lactate/Acetate | Temperature |
|---|---|---|---|---|---|---|
| SM29 | Salami | short rods in chains, Gram-positive | negative | β Gentiobiose, D-Turanose, D-Tagatose Ribose, Adonitol, Galactose, D-Glucose, D-Fructose, D-Mannose, Rhamnose, Dulcitol, Mannitol, Sorbitol, α Metyhl-D-mannoside, α Methyl-D-glucoside, N Acetyl glucosamine, Amygdaline, Arbutine, Esculine, Salicine, Cellobiose, Maltose, Lactose, Saccharose, Trehalose, Inuline, Melezitose, β Gentiobiose, D-Turanose, D-Tagatose | D-, L-Lactate | 15–45° C. (Opt: 32–37° C. |
| SM63 | Raw milk | short rods in chains, Gram-positive | negative | Ribose, Galactose, D-Glucose, D-Fructose. D-Mannose, Mannitol, Sorbitol, N Acetyl glucosamine, Maltose, Lactose, Trehalose, Melezitose, D-Tagatose | D-, L-Lactate | 15–45° C. (Opt.: 32–37° C. |
| SM11 | Raw milk | pleomorphic rod-shaped, Gram-positive | | Erythritol, D-Arabinose, Ribose, Adonitol, Galactose, D-Glucose, D-Fructose, D-Mannose, Lactose, D-Arabitol. | Acetate, Propionate[f] | 15–37° C. (Opt.: 30–32° C. |

| Strain | NaCl Tolerance | Proteolytic activity | Catalase activity | API 50 CHL | Identification Sequencing[c] | PCR[d] |
|---|---|---|---|---|---|---|
| SM20 | 10%[g] | negative | negative | Lactobacillus paracasei subsp. paracasei | <u>Lactobacillus paracasei subsp. paracasei</u>[l] and Lactobacillus casei | <u>Lactobacillus paracasei subsp. paracasei</u> |
| SM29 | 5%[h] | negative | negative | Lactobacillus paracasei subsp. paracasei | <u>Lactobacillus paracasei subsp. paracasei</u> and Lactobacillus casei | Lacotobacillus paracasei subsp. paracasei |
| SM63 | 5%[i] | negative | negative | Lactobacillus curvatus | <u>Lactobacillus paracasei subsp. paracasei</u> and Lactobacillus casei | Lactobacillus paracasei subsp. paracasei |
| SM11 | 5%[k] | negative | positive | | <u>Propionibacterium jensenii</u> | |

[a]determined using API 50 CHL
[b]determined enzymatically (Boehringer Mannheim, Germany; kit used for D/L-lactic acid: E1 112 821/kit used for acetic acid: E0 148 261)
[c]sequencing analysis of the 16S rDNA
[d]PCR approach modified according to Ward and Timmins (1999)
[e]long rods in chains in bioreactor cultures
[f]Miescher (1999)
[g]well growth at a salinity of 5% and fairly well growth at 10%
[h]well growth at a salinity of 5% NaCl and very weak growth at 10%
[i]well growth at a salinity of 5% and weak growth at 10%
[k]fairly well growth at a salinity of 5% NaCl and very weak growth at 10%
[l]underlined species indicates the final identification of the corresponding strain Collins et al. (1989) described another subspecies of *Lactobacillus paracasei*, namely *Lactobacillus paracasei* subsp. *tolerans*. Regarding the acid production observed by Collins et al. (1989), the isolates SM20, SM29 and SM63 belong to the subspecies *paracasei*.

Secretion of Inhibitory Substances into Broth Medium

*Lactobacillus paracasei* subsp. *paracasei* SM20, *Lactobacillus paracasei* subsp. *paracasei* SM29, *Lactobacillus paracasei* subsp. *paracasei* SM63, *Lactobacillus plantarum* SM17 and *Lactobacillus plantarum* SM39 were examined for their ability to secret inhibitory substances into broth medium. Therefore strains were either grown in MRS broth or in SWP1 medium. No antagonistic activity was detected in the cell-free supernatants using a well diffusion test. Even a concentration step by ultrafiltration (molecular weight cut-off of 3'000 Da) did not reveal any detectable activity (data not shown).

Antifungal Activities in Agar Plates

A total of 18 lactobacilli were tested for their antifungal activities alone or in combination with the high-antifungal *Propionibacterium jensenii* SM11. Therefore, the strains were incorporated, after centrifugation and a washing step in concentrations from $10^5$ to $10^8$ cfu/ml in YM agar plates onwhich the fungi listed in Table 1 were spotted in corresponding levels from $10^1$ to $10^7$ cfu/ml. The plates were stored in different batches at 6° C., 12° C. and 25° C. The growth of yeasts was controlled weekly or daily, respectively. Although, the lactobacilli as well as the *Propionibacterium* strain showed only weak inhibitory activities using them alone (data not shown) their combination revealed high antagonistic values at 6° C. The highest activities were detected with the following lactobacilli in combination with *Propionibacterium jensenii* SM11: *Lactobacillus paracasei* subsp. *paracasei* SM20, *Lactobacillus paracasei* subsp. *paracasei* SM29 and *Lactobacillus paracasei* subsp. *paracasei* SM63. Weak activities were observed with *Lactobacillus plantarum* SM17 and *Lactobacillus plantarum* SM39 in conjunction with strain SM11. A cell number of $10^8$ cfu/ml of the *Lactobacillus*-strain and $10^8$ cfu/ml of the *Propionibacterium*-strain was necessary for high inhibitory activities. Table 4 indicates five examples of the antifungal activities observed at 6° C. with a concentration of $10^8$ cfu/ml ($10^7$ cfu/ml for *Lactobacillus plantarum* SM17) against spot-inoculated yeasts in a density of $10^6$ cfu/ml and against spot-inoculated 3-day cultures of moulds.

TABLE 4

Antifungal activities of selected protective cultures incorporated in agar plates after a storage of 21 days at 6° C., or 7 days at 12° C.

| Indicatororganisms[a] | Protective cultures[b] | | | | | | |
|---|---|---|---|---|---|---|---|
| | SM20/SM11 (pH 3.83)[c] | SM29/SM11 (pH 3.98) | SM63/SM11 (pH 3.93) | SMI7/SM11 (pH 4.53) | SM39/SM11 (pH 4.59) | control (pH 5.88) | Ka-Sorbat (lg/l)[d] |
| Storage at 6° C./21 d | | | | | | | |
| *Candida magnoliae* 1-35/1 | + | +/− | + | ++ | ++ | ++ | ++ |
| *Candida parapsilosis* 4-5/1 | − | − | − | − | − | (+/−) | − |
| *Zygosacharomyces bailii* 1-48/1 | − | − | − | − | − | − | − |
| *Candida silvicola* 4-42/1 | (+/−) | (+/−) | (+/−) | ++ | ++ | ++ | ++ |
| *Candida valida* 1-48/8 | (+/−) | (+/−) | (+/−) | ++ | ++ | + | − |
| *Candida pulcherrima* 1-50/13 | (+/−) | − | (+/−) | ++ | ++ | ++ | ++ |
| *Candida reukaufii* 4-73/4 | − | − | − | ++ | ++ | ++ | ++ |
| *Candida* sp. 1-50/15 | (+/−) | (+/−) | (+/−) | ++ | ++ | ++ | ++ |
| *Sporobolomyces salmonicolor* 3-46/2 | − | − | − | − | − | ++ | − |
| *Candida krusei* 3-69/2 | − | − | − | (+/−) | (+/−) | (+/−) | − |
| *Penicillium* sp. 2-21/7 | − | − | − | n.d. | n.d. | ++ | n.d. |
| *Penicillium* sp. 2-21/12 | − | − | − | n.d. | n.d. | ++ | n.d. |
| *Penicillium* sp. 2-52/2 | − | − | − | n.d. | n.d. | ++ | n.d. |
| *Penicillium* sp. 3-58/3 | − | − | − | n.d. | n.d. | ++ | n.d. |
| Storage at 12° C./7 d | | | | | | | |
| *Candida magnoliae* 1-35/1 | (+/−) | + | + | + | + | ++ | n.d |
| *Candida parapsilosis* 4-5/1 | − | (+/−) | − | +/− | +/− | ++ | n.d |
| *Zygosacharomyces bailii* 1-48/1 | − | (+/−) | (+/−) | (+/−) | − | +/− | n.d |
| *Candida silvicola* 4-42/1 | (+/−) | (+/−) | (+/−) | (+/−) | (+/−) | ++ | n.d |
| *Candida valida* 1-48/8 | − | + | + | ++ | + | ++ | n.d |
| *Candida pulcherrima* 1-50/13 | − | ++ | + | ++ | ++ | ++ | n.d |
| *Candida reukaufii* 4-73/4 | − | + | − | ++ | ++ | ++ | n.d |
| *Candida* sp. 1-50/15 | − | ++ | ++ | ++ | ++ | ++ | n.d |
| *Sporobolomyces salmonicolor* 3-46/2 | − | − | − | + | +/− | +/+ | n.d |
| *Candida krusei* 3-69/2 | + | ++ | ++ | ++ | ++ | ++ | n.d |

SM20: *Lactobacillus paracasei* subsp. *paracasei* SM20 ($10^8$ cfu/ml)
SM29: *Lactobacillus paracasei* subsp. *paracasei* SM29 ($10^8$ cfu/ml)
SM63: *Lactobacillus paracasei* subsp. *paracasei* SM63 ($10^8$ cfu/ml)
SM17: *Lactobacillus plantarum* SM17 ($10^7$ cfu/ml)
SM39: *Lactobacillus plantarum* SM39 ($10^7$ cfu/ml)
SM11: *Propionibacterium jensenii* SM11 ($10^8$ cfu/ml)
n.d.: not determined
[a]spot-inoculation with $10^6$ cfu/ml
[b]incorporated in agar plates
[c]pH measured on agar plates after a storage of 21 days at 6° C.
[d]concentration according to EU-Richlinie, Nr. 95/2/EG
+ normal colony (≈25% inhibition)
++ strong colony (≈0% inhibition)
+/− weak colony (≈50% inhibition)
(+/−) very weak colony (≈75% inhibition)
− no colony (≈100% inhibition)

Interestingly, using Ka-Sorbat, a weaker inhibitory activity was observed at 6° C. than with the antimicrobial cultures of this study (strains SM20, SM29 or SM63 in combination with strain SM11). Table 4 further depicts, that after a storage of 7 days at 12° C. a clear inhibitory activity was observed for *Lactobacillus paracasei* subsp. *paracasei* strains SM20, SM29 and SM63 and a weak for *Lactobacillus plantarum* strains SM17 and SM39 in conjunction with *Propionibacterium jensenii* SM11. At 25° C. only weak inhibitory activities were observed that disappeared after a few days (data not shown). Testing the antifungal activities of 2 or 3 lactobacilli (*Lactobacillus paracasei* subsp. *paracasei* strains SM20, SM29 and SM63) in conjunction with *Propionibacterium jensenii* SM11, an increase in inhibition was observed (Table 5) in comparison with the trials in which 1 *Lactobacillus* strain in combination with SM11 was used (Table 4). A total inhibition of the yeasts was reached using *Lactobacillus paracasei* subsp. *paracasei* strains SM20, SM29 or SM63 in conjunction with *Propionibacterium jensenii* SM11 and 1 g/l Ka-Sorbat (Table 5). The antifungal activity of the bacterial strains was increased with the food preservative.

TABLE 5

Antifungal activities of selected protective cultures incorporated in agar plates after a storage of 21 days at 6° C.

| Indicatororganisms[a] | Protective cultures[b] | | | | | | | |
|---|---|---|---|---|---|---|---|---|
| | SM20/SM29/SM11 (pH 4.27)[c] | SM20/SM63/SM11 (pH 4.32) | SM29/SM63/SM11 (pH 4.33) | SM20/SM29/SM63/SM11 (pH 4.10) | SM20/SM11/Ka-Sorbat[d] (pH 4.67) | SM29/SM11/Ka-Sorbat (pH 4.80) | SM63/SM11/Ka-Sorbat (pH 4.75) | control (pH 6.04) |
| *Candida magnoliae* 1-35/1 | (+/−) | (+/−) | +/− | (+/−) | − | − | − | ++ |
| *Candida parapsilosis* 4-5/1 | − | − | − | − | − | − | − | − |
| *Zygosacharomyces bailii* 1-48/1 | − | − | − | − | − | − | − | − |
| *Candida silvicola* 4-42/1 | − | − | − | − | − | − | − | ++ |
| *Candida valida* 1-48/8 | − | − | (+/−) | − | − | − | − | (+/−) |
| *Candida pulcherrima* 1-50/13 | − | − | (+/−) | − | − | − | − | ++ |
| *Candida reukaufii* 4-73/4 | − | − | − | − | − | − | − | ++ |
| *Candida* sp. 1-50/15 | − | − | (+/−) | − | − | − | − | + |
| *Sporobolomyces salmonicolor* 3-46/2 | − | − | − | − | − | − | − | +/− |
| *Candida krusei* 3-69/2 | − | − | − | − | − | − | − | − |

SM20: *Lactobacillus paracasei* subsp. *paracasei* SM20 ($10^8$ cfu/ml)

SM29: *Lactobacillus paracasei* subsp. *paracasei* SM29 ($10^8$ cfu/ml)

SM63: *Lactobacillus paracasei* subsp. *paracasei* SM63 ($10^8$ cfu/ml)

SM11: *Propionibacterium jensenii* SM11 ($10^8$ cfu/ml)

n.d.: not determined

[a]spot-inoculation with $10^6$ cfu/ml

[b]incorporated in agar plates

[c]pH measured on agar plates after a storage of 21 days at 6° C.

[d]1 g/l, concentration according to EU-Richtlinie, Nr. 95/2/EG

++ strong colony (≈0% inhibition)

+ normal colony (≈25% inhibition)

+/− weak cololny (≈50% inhibition)

(+/−) very weak colony (≈75% inhibition)

− no colony (≈100% inhibition)

Antibacterial Activities of Protective Cultures in Agar Plates

*Lactobacillus paracasei* subsp. *paracasei* strains SM20, SM29 and SM63 were further tested for their ability to inhibit Gram-positive and Gram-negative bacteria alone or in combination with *Propionibacterium jensenii* SM11. Therefore, the strains were incorporated after centrifigation and a washing step in a concentration of $10^8$ cfu/ml in BHI agar plates on which overnight cultures of the corresponding bacteria were spotted. One batch of the plates was stored at 6° C. and the growth of bacteria was controlled weekly, a second was incubated at 25° C. and was daily scored for inhibition. Again, the lactobacilli as well as the *Propionibacterium* strain showed weak inhibitory activities using them alone (data not shown) but their combination revealed high antagonistic values (Table 6).

TABLE 6

Antibacterial activities of selected protective cultures incorporated in agar plates after a storage of 21 days at 6° C. or at 25° C.

| | Protective cultures[b] | | | |
|---|---|---|---|---|
| Indicatororganisms[a] | SM20/SM11 (pH 5.45[c]) | SM29/SM11 (pH 5.48) | SM63/SM11 (pH 5.40) | control (pH 6.70) |
| Storage at 6° C./21 d | | | | |
| *Listeria innocua* L17 | − | − | − | ++ |
| *Staphylococcus aureus* VF4 | − | − | − | (+/−) |
| *Escherichia coli* B | − | − | − | (+/−) |
| *Escherichia coli* SG63 | − | − | − | +/− |
| *Sereratia liquefaciens* SG64 | − | (+/−) | + | ++ |
| *Citrobacter freundii* SG84 | (+/−) | (+/−) | (+/−) | ++ |
| *Klebsiella pneumoniae* SG89 | (+/−) | (+/−) | +/− | ++ |
| *Enterobacter cloacae* SG95 | (+/−) | (+/−) | (+/−) | + |
| *Enterococcus faecalis* DS5 | − | − | − | + |
| *Bacillus subtilis* 168 | − | − | − | − |
| *Bacillus cereus* DSM 31[τ] | − | − | − | − |
| *Salmonella typhimurium* ATCC 14058 | − | − | − | ++ |
| *Listeria monocytogenes* M1 | − | − | − | ++ |
| Storage at 25° C./21 d | | | | |
| *Listeria innocua* L17 | − | − | − | ++ |
| *Staphylococcus aureus* VF4 | + | +/− | +/− | ++ |
| *Escherichia coli* B | + | (+/−) | (+/−) | ++ |
| *Escherichia coli* SG63 | +/− | − | − | ++ |
| *Sereratia liquefaciens* SG64 | +/− | + | +/− | ++ |
| *Citrobacter freundii* SG84 | (+/−) | +/− | (+/−) | ++ |
| *Klebsiella pneumoniae* SG89 | (+/−) | +/− | + | ++ |
| *Enterobacter cloacae* SG95 | (+/−) | + | + | ++ |
| *Enterococcus faecalis* DS5 | (+/−) | (+/−) | (+/−) | ++ |
| *Bacillus subtilis* 168 | − | − | − | ++ |
| *Bacillus cereus* DSM 31[τ] | − | (+/−) | (+/−) | ++ |
| *Salmonella typhimurium* ATCC 14028 | − | − | − | ++ |
| *Listeria monocytogenes* M1 | − | − | − | ++ |

SM20: *Lactobacillus paracasei* subsp. *paracasei* SM20 ($10^8$ cfu/ml)
SM29: *Lactobacillus paracasei* subsp. *paracasei* SM29 ($10^8$ cfu/ml)
SM63: *Lactobacillus paracasei* subsp. *paracasei* SM63 ($10^8$ cfu/ml)
SM11: *Propionibacterium jensenii* SM11 ($10^8$ cfu/ml)

[a]spot-inoculation with an overnight culture

[b]incorporated in agar plates

[c]pH measured on agar plates after a storage of 21 days at 6° C.

++ strong colony (≈0% inhibition)

(+/−) very weak colony (≈75% inhibition)

+ normal colony (≈25% inhibition)

− no colony (≈100% inhibition)

+/− weak cololny (≈50% inhibition)

Antifungal Activities of Stored Protective Cultures

In order to determine the ability to store the protective cultures, they were held separately at a 100-fold concentration (resuspended in tydallized skim milk) at −80° C. for 15 weeks. Then, the strains were incorporated in a concentration of $10^8$ cfu/ml in YM agar plates on which the yeasts listed in Table 1 were spotted in levels from $10^4$ to $10^7$ cfu/ml. The plates were stored at 6° C. and growth of yeasts was controlled weekly. As a control, an agar plate was prepared with an addition of an appropriate amount of skim milk. Table 7 shows in a summary, that the protective cultures consisting of *Propionibacterium jensenii* SM11 and a *Lactobacillus paracasei* subsp. *paracasei* strain (SM20, SM29 or SM63) still showed unchanged antifungal activities after a storage of 15 weeks at −80° C.

*tobacillus paracasei* subsp. *paracasei* SM63 showed an increase in yeasts. The level of propionibacteria and lactobacilli neither increased nor decreased during storage. The pH of samples with protective cultures did not show any significant differences to the control sample (data not shown).

Antifungal Activities in Yoghurt

A further trial was set up with yoghurt and protective cultures consisting of *Lactobacillus paracasei* subsp. *paracasei* strains SM20, SM29 or SM63 in combination with *Propionibacterium jensenii* SM11. Therefore, a milk enriched with nutrients was used that should favour the growth of contaminating yeasts. This milk was fermented with a commercial yoghurt culture in the presence of a protective culture. The protective cultures were used at concentrations of $10^7$ cfu/g or $10^8$ cfu/g, respectively. After fermen-

TABLE 7

Antifungal activities of selected protective cultures after a storage of 15 weeks at −80° C., incorporated in agar plates.

| Indicatororganisms[a] | Protective cultures[b] | | | |
|---|---|---|---|---|
| | SM20/SM11 | SM29/SM11 | SM63/SM11 | control |
| *Candida magnoliae* 1-35/1 | +/− | +/− | +/− | ++ |
| *Candida parapsilosis* 4-5/1 | − | − | − | (+/−) |
| *Zygosaccharomyces bailii* 1-48/1 | − | − | − | − |
| *Candida silvicola* 4-42/1 | − | − | − | ++ |
| *Candida valida* 1-48/8 | + | + | + | + |
| *Candida pulcherrima* 1-50/13 | +/− | +/− | + | ++ |
| *Candida reukaufii* 4-73/4 | − | − | − | ++ |
| *Candida* sp. 1-50/15 | + | + | + | ++ |
| *Sporobolomyces salmonicolor* 3-46/2 | − | − | − | +/− |
| *Candida krusei* 3-69/2 | − | − | − | − |

SM20: *Lactobacillus paracasei* subsp. *paracasei* SM20 ($10^8$ cfu/ml)
SM29: *Lactobacillus paracasei* subsp. *paracasei* SM29 ($10^8$ cfu/ml)
SM63: *Lactobacillus paracasei* subsp. *paracasei* SM63 ($10^8$ cfu/ml)
SM11: *Propionibacterium jensenii* SM11 ($10^8$ cfu/ml)
n.d.: not determined
[a]spot-inoculation with $10^6$ cfu/ml
[b]incorporated in agar plates
++ strong colony (≈0% inhibition)
+ normal colony (≈25% inhibition)
+/− weak cololny (≈50% inhibition)
(+/−) very weak colony (≈75% inhibition)
− no colony (≈100% inhibition)

Antifungal Activities of Protective Cultures in a Food Model

Figure 3:
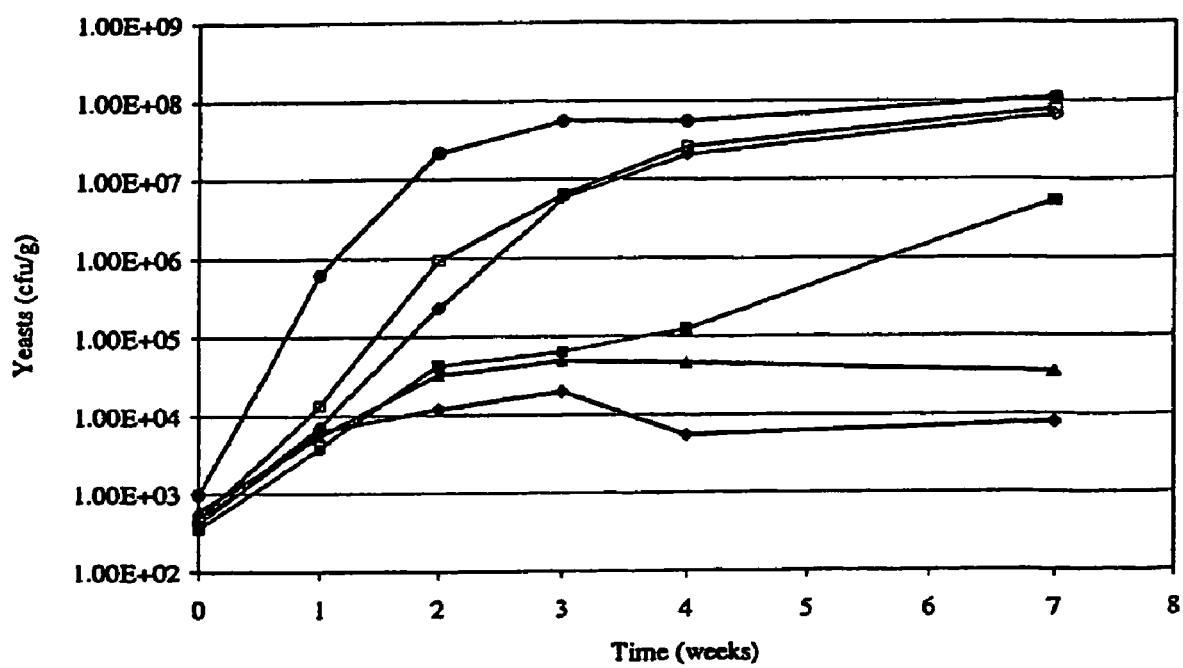
FIG. 3: Levels of yeasts (*Candida pulcherrima* 1-50/13) in 5 different batches of a food model with different protective cultures, stored at 6° C. (♦) 4.9×10$^8$ cfu/g *Propionibacterium jensenii* SM11 and 1.2×10$^8$ cfu/g *Lactobacillus paracasei* ssp. *paracasei* SM20; (▲) 3.2×10$^8$ cfu/g *Propionibacterium jensenii* SM11 and 1.1×10$^8$ cfu/g *Lactobacillus paracasei* ssp. *paracasei* SM29; (■) 4.1×10$^8$ cfu/g *Propionibacterium jensenii* SM11 and 9.1×10$^7$ cfu/g *Lactobacillus paracasei* subsp. *paracasei* SM63; (□) 2.7×10$^8$ cfu/g *Propionibacterium jensenii* SM11 and 2.1×10$^8$ cfu/g *Lactobacillus plantarum* SM17; (◇) 2.7×10$^8$ cfu/g *Propionibacterium jensenii* SM11 and 9.3×10$^7$ cfu/g *Lactobacillus plantarum* SM39; (●) no protective culture. Number of yeasts are mean values of duplicates.
Figure 4:
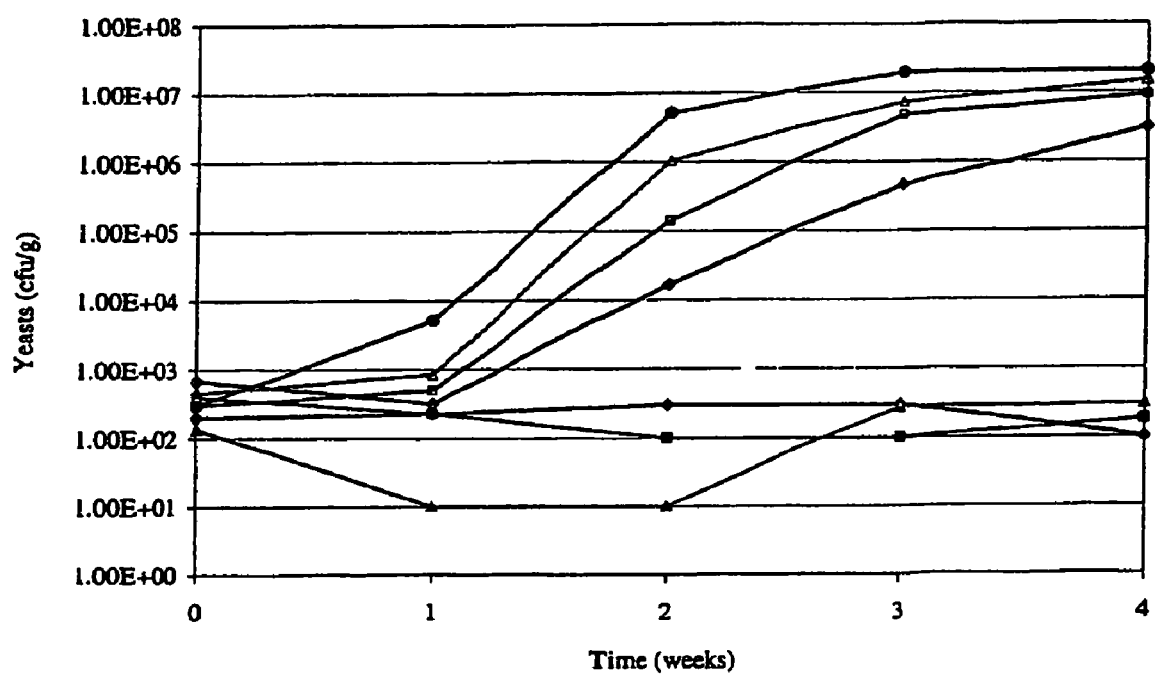
FIG. 4: Levels of yeasts (*Candida pulcherrima* 1-50/13, *Candida magnoliae* 1-35/1, *Candida parapsilosis* 4-5/1 and *Zygosaccharomyces bailii* 1-48/1) in 7 different batches of yoghurt with different protective cultures stored at 6° C. (◇) 1.5×10$^7$ cfu/g *Propionibacterium jensenii* SM11 and 4.3×10$^7$ cfu/g *Lactobacillus paracasei* ssp. *paracasei* SM20; (♦) 5.5×10$^7$ cfu/g *Propionibacterium jensenii* SM11 and 1.7×10$^8$ cfu/g *Lactobacillus paracasei* ssp. *paracasei* SM20; (□) 2.0×10$^7$ cfu/g *Propionibacterium jensenii* SM11 and 3.8×10$^7$ cfu/g *Lactobacillus paracasei* ssp. *paracasei* SM29; (■) 2.8×10$^8$ cfu/g *Propionibacterium jensenii* SM11 and 1.7×10$^8$ cfu/g *Lactobacillus paracasei* ssp. *paracasei* SM29; (Δ) 1.6×10$^7$ cfu/g *Propionibacterium jensenii* SM11 and 1.7×10$^7$ cfu/g *Lactobacillus paracasei* ssp. *paracasei* SM63; (▲) 8.1×10$^7$ cfu/g *Propionibacterium jensenii* SM11 and 1.6×10$^8$ cfu/g *Lactobacillus paracasei* ssp. *paracasei* SM63; (●) no protective culture. Number of yeasts are mean values of duplicates.

For a preliminary trial, a food model was set up with different protective cultures. The antagonistic strains were added to tyndallized skim milk at initial levels of $10^8$ cfu/g. They were *Lactobacillus paracasei* subsp. *paracasei* SM20, *Lactobacillus paracasei* subsp. *paracasei* SM29, *Lactobacillus paracasei* subsp. *paracasei* SM63, *Lactobacillus plantarum* SM17 and *Lactobacillus plantarum* SM39 in combination with *Propionibacterium jensenii* SM11. Additionally the samples were inoculated with *Candida pulcherrima* 1-50/13 at levels of $10^2$ cfu/g and then stored at 6° C. As indicated in FIG. 3, the levels of yeasts increased constantly to $10^7$-$10^8$ cfu/g in the samples with the *Lactobacillus plantarum* strains SM17 and SM39 as well as in the control sample showing the highest values. Samples containing *Lactobacillus paracasei* subsp. *paracasei* (SM20, SM29 or SM63) showed significant differences. In these samples, *Candida pulcherrima* 1-50/13 increased up to a level of $10^4$ cfu/g and then remained almost stable for seven weeks. After four weeks samples with *Lac-* tation and cooling down, the samples were inoculated with a mix of *Candida pulcherrima* 1-50/13, *Candida magnoliae* 1-35/1, *Candida parapsilosis* 4-5/1 and *Zygosaccharomyces bailii* 1-48/1 at a level of $10^2$ cfu/g and then stored at 6° C. FIG. 4 shows that the levels of yeasts in samples with protective cultures at a concentration of $10^7$ cfu/g as well as in the control sample increased constantly. Nevertheless, the control sample always showed the highest values of contaminating yeasts. In all samples containing the protective cultures at a level of $10^8$ cfu/g no increase of yeasts was observed. The level of yeasts remained stable over a period of 4 weeks. The same phenomenon was observed with concentrations of 1.7× $10^8$ cfu/g lactobacilli and 5.5×$10^7$ cfu/g propionibacteria (Table 11). In all samples, the levels of protective culture neither increased nor decreased during storage. The pH of samples with protective cultures did not show any significant differences to the control sample (data not shown). As shown in Table 8, in samples with protective cultures 60-70 mg/100 g acetate were enzymatically determined whereas only 4.43 mg/100 g were detected in the control sample without protective culture.

TABLE 8

Enzymatically determined concentrations of organic acids metabolised in yoghurt with protective cultures.

| | Organic acids | | | |
|---|---|---|---|---|
| Protective cultures | Acetate (mg/100 g) | D-Lactate (g/100 g) | L-Lactate (g/100 g) | Total lactate (g/100 g) |
| SM20/SM11[a] | 68.84 | 0.01 | 0.61 | 0.62 |
| SM29/SM11[b] | 60.95 | 0.01 | 0.62 | 0.63 |
| SM63/SM11[c] | 61.44 | 0.01 | 0.65 | 0.66 |
| control[d] | 4.43 | 0.01 | 0.74 | 0.75 |

SM20: *Lactobacillus paracasei* subsp. *paracasei* SM20
SM29: *Lactobacillus paracasei* subsp. *paracasei* SM29
SM63: *Lactobacillus paracasei* subsp. *paracasei* SM63
SM11: *Propionibacterium jensenii* SM11
[a]SM20, $1.7 \times 10^8$ cfu/g; SM11, $5.5 \times 10^7$ cfu/g
[b]SM29, $1.7 \times 10^8$ cfu/g; SM11, $2.8 \times 10^8$ cfu/g
[c]SM63, $1.6 \times 10^8$ cfu/g; SM11, $8.1 \times 10^7$ cfu/g
[d]no protective culture In contrast, the protective culture did not influence the content of D-lactate, L-lactate as well as total lactate (Table 8).

Using different sensory test, the yoghurts with protective cultures and the control samples without an additional culture did not show any perceptible differences after storage periods of 5 and 15 days.

Scale Up of the Application of a Protective Culture to Yoghurt

The scale up trials with yoghurt gave similar results as were obtained by the trials on laboratory scale.

Antifungal Activities on the Cheese Surface

Table 9 shows the inhibition of a mix of yeasts on cheese surfaces, treated with three different protective cultures at different concentrations. The cheeses were all contaminated with yeasts to reach a final level on the surface of $10^2$ cfu/g. The surface of the cheeses was defined as a layer of about 3 mm from the outside of the cube.

TABLE 9

Inhibition of yeasts on cheese surfaces held at 6° C.

| | | cfu/g of yeasts[a] | | |
|---|---|---|---|---|
| | Time (days) | A | B | C |
| K1 | 1 | $5.0 \times 10^2$ | $3.2 \times 10^2$ | $4.1 \times 10^2$ |
| | 21 | $1.5 \times 10^2$ | $<10^2$ | $<10^2$ |
| K2 | 1 | $5.5 \times 10^2$ | $1.0 \times 10^2$ | $4.1 \times 10^2$ |
| | 21 | $3.5 \times 10^2$ | $<10^2$ | $<10^2$ |
| K3 | 1 | $2.2 \times 10^3$ | $2.7 \times 10^2$ | $1.3 \times 10^3$ |
| | 21 | $1.3 \times 10^4$ | $<10^2$ | $1.0 \times 10^2$ |
| K4 | 1 | $6.3 \times 10^2$ | | |
| | 21 | $8.0 \times 10^3$ | | |

A: inoculated with yeasts and protective culture SM20/SM11
B: inoculated with yeasts and protective culture SM29/SM11
C: inoculated with yeasts and protective culture SM63/SM11
K1: concentration of protective culture: $10^7$–$10^8$ cfu/g surface
K2: concentration of protective culture: $10^6$–$10^7$ cfu/g surface
K3: concentration of protective culture: approx. $10^6$ cfu/g surface
K4: control, inoculated with yeasts, no protective culture added
[a]a mix of *Candida pulcherrima* 1-50/13, *Candida magnoliae* 1-35/1, *Candida parapsilosis* 4-5/1 and *Zygosaccharomyces bailii* 1-48/1

At concentrations of $10^8$ and $10^7$ cfu/g surface, the protective cultures were able to inhibit the outgrowth of yeasts totally during a storage of 21 days at 6° C. The number of yeasts even declined (K1, K2). A level of $3.0 \times 10^6$ cfu/g surface of lactobacilli and $3.0 \times 10^6$ cfu/g surface of propionibacteria seemed to be the limit to reach a minimal inhibition of the yeasts. Cheese sample K3A showed lower levels of protective culture and did thus not inhibit the outgrowth of the contaminating yeasts. The levels of protective cultures in the surfaces of the cheeses were in the same range as the cell numbers of the solutions in which the cheeses had previously been soaked (data not shown).

Inhibition of *Listeria* in Food Models with Protective Cultures

Table 10 summarises the inhibition of *Listeria* with protective cultures in minced meat and cream.

TABLE 10

Inhibition of *Listeria* by protective cultures in food models held at 6° C. and 25° C.

| Food systems | Time (days) | A | B | C | D |
|---|---|---|---|---|---|
| | | cfu/g of *Listeria innocua* L17 | | | |
| Minced | 1 | $3.3 \times 10^3$ | $2.8 \times 10^3$ | $2.6 \times 10^3$ | $2.7 \times 10^3$ |
| meet | 28 | $6.0 \times 10^2$ | $3.7 \times 10^2$ | $2.7 \times 10^2$ | $4.5 \times 10^2$ |
| (6° C.) | 42 | $1.7 \times 10^3$ | $<10^2$ | $1.5 \times 10^2$ | $<10^2$ |
| | 56 | $5.1 \times 10^3$ | $8.2 \times 10^2$ | $<10^2$ | $1.5 \times 10^2$ |
| Minced | 0 | $4.1 \times 10^3$ | $4.9 \times 10^3$ | $4.0 \times 10^3$ | $3.7 \times 10^3$ |
| meet | 2 | $4.5 \times 10^3$ | $5.5 \times 10^3$ | $3.0 \times 10^3$ | $7.5 \times 10^3$ |
| (25° C.) | 5 | $6.8 \times 10^4$ | $5.9 \times 10^3$ | $3.2 \times 10^3$ | $5.5 \times 10^3$ |
| Cream | 1 | $2.7 \times 10^3$ | $3.2 \times 10^3$ | n.d. | n.d. |
| (6° C.) | 14 | $1.3 \times 10^3$ | $1.2 \times 10^3$ | n.d. | n.d. |
| | 21 | $1.1 \times 10^3$ | $1.5 \times 10^2$ | n.d. | n.d. |
| | 28 | $1.0 \times 10^3$ | $<10^2$ | n.d. | n.d. |
| Cream | 1 | $2.9 \times 10^2$ | $2.6 \times 10^2$ | $2.2 \times 10^2$ | $3.0 \times 10^2$ |
| (25° C.) | 21 | $10^7$–$10^8$ | $<10^2$ | $<10^2$ | $<10^2$ |
| | | cfu/g of *Listeria monocytogenes* M1 | | | |
| Cream | 1 | $1.6 \times 10^3$ | $1.7 \times 10^3$ | n.d. | n.d. |
| (6° C.) | 7 | $2.9 \times 10^7$ | $1.9 \times 10^3$ | n.d. | n.d. |
| | 14 | $3.0 \times 10^8$ | $7.5 \times 10^2$ | n.d. | n.d. |

A: control, inoculated with *Listeria* no protective culture added
B: inoculated with *Listeria* and protective culture SM20/SM11
C: inoculated with *Listeria* and protective culture SM29/SM11
D: inoculated with *Listeria* and protective culture SM63/SM11
n.d.: not determined The two food models were selected to represent high moisture-food with different fat and protein contents and an optimal pH for *Listeria*. Although *Listeria innocua* L17 showed good growth after 21 days on BHI agar stored at 6° C. (Table 6), it was not detected in the food models. The viable numbers of the indicator organism, however, decreased in the presence of a protective culture. Furthermore, these samples still showed a nice red meat colour after a storage of 56 days and the control sample was green to brown and clearly spoiled. The pH of the control sample was 6.20 after 56 days that one of the samples with protective cultures in a range of 5.50 to 5.81. The level of propionibacteria and lactobacilli remained unchanged during the storage at 6° C. for a period of 56 days. A second charge of minced meat with and without protective cultures was stored at 25° C. After a storage of 5 days, *Listeria innocua* L17 was held in check in the samples with protective cultures (3.2 to $5.9 \times 10^3$ cfu/g) whereas the viable number of the indicator organism increased to $6.8 \times 10^4$ cfu/g in the control sample. Additionally, the control sample had totally gone bad. The cream stored at 6° C. showed the same phenomenon after 28 days. In the control sample, the number of *Listeria innocua* L17 was still in the same range as in the beginning ($10^3$ cfu/g) but in the sample with protective culture, the viable number of the indicator organism went down to under $10^2$ cfu/g. The level of lactobacilli and propionibacteria neither increased nor descresed during storage. The pH values in the samples with or without protective culture were in the same range. After a storage of 28 days at 6° C. the pH of the cream has gone down to 4.78 in the sample without protective culture and to 4.60 in the sample with protective culture. In cream samples stored at 25° C. *Listeria innocua* L17 decreased below $10^2$ cfu/g in the presence of protective cultures but went up to a cell number of $10^7$-$10^8$ cfu/g in the control sample. Similarly the pH of these samples changed clearly. The samples with protective cultures were in a range of 3.56-3.68, whereas the control sample still had a pH of 5.80. After 21 days of storage at 25° C., the cell numbers of lactobacilli and propionibacteria were still in the same range as at the beginning. The levels of protective cultures neither increased nor decreased. In the samples with *Listeria monocytogenes* M1 as indicator organism a clear difference in the viable number of the pathogen was observed in the presence or absence of the protective culture. After a storage of 14 days at 6° C., the sample without protective culture contained $3.0 \times 10^8$ cfu/g of *Listeria monocytogenes* M1 whereas in the sample with the protective culture the number of the indicator organism had even decreased to $7.5 \times 10^2$ cfu/g (Table 10).

Necessary Concentration of Protective Culture in Food for a Sufficient Antimicrobial Activity To reach a sufficient antimicrobial activity, a certain level of lactobacilli and propionibacteria was necessary. Tables 11 and 12 show the different trials of this study and the corresponding levels of protective culture.

TABLE 11

Levels of protective cultures used in the different trials to detect antifungal activities (cfu/g).

| | Trials | | | | | | | |
|---|---|---|---|---|---|---|---|---|
| | Agarplates[a] | | Food Model | | Yoghurt[b] | | Yoghurt[c] | |
| Cultures | LB | PAB | LB | PAB | LB | PAB | LB | PAB |
| SM20/SM11 | $10^8$ | $10^8$ | $1.2 \times 10^8$ | $4.9 \times 10^8$ | $1.7 \times 10^8$ | $5.5 \times 10^7$ | $4.3 \times 10^7$ | $1.5 \times 10^7$ |
| SM29/SM11 | $10^8$ | $10^8$ | $1.1 \times 10^8$ | $3.2 \times 10^8$ | $1.7 \times 10^8$ | $2.8 \times 10^8$ | $3.8 \times 10^7$ | $2.0 \times 10^7$ |
| SM63/SM11 | $10^8$ | $10^8$ | $9.1 \times 10^7$ | $4.1 \times 10^8$ | $1.6 \times 10^8$ | $8.1 \times 10^7$ | $1.7 \times 10^7$ | $1.6 \times 10^7$ |

SM20: *Lactobacillus paracasei* subsp. *paracasei* SM20
SM29: *Lactobacillus paracasei* subsp. *paracasei* SM29
SM63: *Lactobacillus paracasei* subsp. *paracasei* SM63
SM11: *Propionibacterium jensenii* SM11
LB: lactobacilli
PAB: propionibacteria
n.d. not determined
[a]level of the protective culture was only determined empirically
[b](1% of each strain in a 100-fold concentration)
[c](0.1% of each strain in a 100-fold concentration)

TABLE 12

Levels of protective cultures used in the different trials to detect antibacterial activities (cfu/g).

| | Trials | | | | | | | | | |
|---|---|---|---|---|---|---|---|---|---|---|
| | Agarplates[a] | | Minced meat[b] | | Minced meat[c] | | Creme[d] | | Creme[e] | |
| Cultures | LB | PAB | LB | PAB | LB | PAB | LB | PAB | LB | PAB |
| SM20/SM11 | $10^8$ | $10^8$ | $1.1 \times 10^9$ | $6.3 \times 10^9$ | $4.8 \times 10^8$ | $2.9 \times 10^8$ | $9.3 \times 10^8$ | $3.8 \times 10^9$ | $1.0 \times 10^9$ | $5.7 \times 10^9$ |
| SM29/SM11 | $10^8$ | $10^8$ | $1.2 \times 10^9$ | $8.1 \times 10^9$ | $4.9 \times 10^8$ | $4.0 \times 10^8$ | n.d. | n.d. | n.d. | n.d. |
| SM63/SM11 | $10^8$ | $10^8$ | $1.6 \times 10^8$ | $8.7 \times 10^9$ | $1.2 \times 10^8$ | $3.0 \times 10^8$ | n.d. | n.d. | n.d. | n.d. |

SM20: *Lactobacillus paracasei* subsp. *paracasei* SM20
SM29: *Lactobacillus paracasei* subsp. *paracasei* SM29
SM63: *Lactobacillus paracasei* subsp. *paracasei* SM63
SM11: *Propionibacterium jensenii* SM11
LB: lactobacilli
PAB: propionibacteria
n.d. not determined
[a]level of the culture was only determined empirically
[b]minced meat stored at 6° C. with *Listeria innocua* L17
[c]minced meat stored at 25° C. with *Listeria innocua* L17
[d]creme stored at 6° C. with *Listeria innocua* L17
[e]creme stored at 6° C. with *Listeria monocytogenes* M1

To reach thus an optimal antifungal activity of the protective culture a level of at least $1.7 \times 10^8$ cfu/g or cfu/ml of lactobacilli in conjunction with $5.5 \times 10^7$ cfu/g or cfu/ml of propionibacteria were necessary (Table 11). On the cheese surface, a level of $1.0 \times 10^7$ cfu/g surface of lactobacilli and $5.0 \times 10^6$ cfu/g surface of propionibacteria seemed to be the minimal concentration to reach a constant satisfactory antifungal activity (data not shown). For a sufficient antibacterial activity, the lowest level tested was $1.2 \times 10^6$ cfu/g or cfu/ml of lactobacilli in conjunction with $3.0 \times 10^8$ cfu/g or cfu/ml of propionibacteria showing still good inhibitory properties (Table 12). According to hitherto investigations the antimicrobial activities are in the same range as the antifungal.

While there are shown and described presently preferred embodiments of the invention, it is to be distinctly understood that the invention is not limited thereto but may be otherwise variously embodied and practiced within the scope of the following claims.

REFERENCES

Al-Zoreky, M. H., J. W. Ayres and W. E. Sandine. 1991. Antimicrobial activity of Microgard™ against food spoilage and pathogenic microorganisms. J. Dairy Sci. 74: 758-763.

Amann, R. I., W. Ludwig, K.-H. Schleifer. 1995. Phylogenetic identification and in situ detection of individual microbial cells without cultivation. Microbiol. Rev. 59: 143-169.

Collins, M. D., B. A. Phillips and P. Zanoni. 1989. Deoxyribonucleic acid homolgy studies of *Lactobacillus casei, Lactobacillus paracasei* sp. nov., subsp. *paracasei* and subsp. *tolerans* and *Lactobacillus rhamnosus* sp. nov., comb. nov. Int. J. Syst. Bacteriol. 39: 105-108.

Daeschel, N. A. 1989. Antimicrobial substances from lactic acid bacteria for use as food preservatives. Food Technol. 43: 164-167.

Daeschel, N. A. 1992. Procedures to detect antimicrobial activities of microorganisms. In Food bio-preservatives of microbiological origin. (R. Bibek and M. A. Daeschel eds.). CRC Press, Inc. Boca Raton, Ann Arbor, London and Tokyo. 57-80.

Dasen, G., J. Smutny, M. Teuber and L. Meile. 1998. Classification and identification of Propionibacteria based on ribosomal RNA genes and PCR. System. Appl. Microbiol. 21: 251-259.

EU-Richtlinie Nr. 95/2/EG des Europäischen Parlaments und des Rats vom 20. Februar 1995 über andere Lebensmittelzusatzstoffe, Farbstoffe und Süssungsmittel.

Federal Register. 1988. Nisin preparation: affirmation of GRAS status as a direct human food ingredient. 21 CFR Part 184, volume 53: 11247-11251.

Goldenberger, D. 1997. Detection of bacterial pathogens in clinical specimen by broad-range PCR amplification and direct sequencing of part of the 16S rRNA gene. PhD thesis No. 12219, ETH, Zurich, Switzerland.

Greisen, K., M. Loeffelholz, A. Purohit and D. Leon. 1994. PCR primers-and probes for the 16S rRNA gene of most species of pathogenic bacteria, including bacteria found in cerebrospinal fluid. J. Clinic. Microbiol. 32: 335-351.

Grinstead, D. A. and S. F. Barefoot. 1992. Jenseniin G, a heat-stable bacteriocin produced by *Propionibacterium jensenii* P126. Appl. Environ. Microbiol. 58: 215-220.

Holzapfel, W. H., R. Geisen and U. Schillinger. 1995. Review Paper. Biological preservation of foods with reference to protective cultures, bacteriocins and food-grade-enzymes. Int. J. Food Microbiol. 24: 343-362.

Jung, G. 1991. Lantibiotics: a survey. In Nisin and novel lantibiotics (Jung, G. and H.-G. Sahl, eds.). Escom Publishers, Leiden, The Netherlands. 1-34.

Lane, D. J. 1991. 16S/23S rRNA sequencing. In: Nucleic acid techniques in bacterial systematics. (Stackebrandt, E. and M. Goodfellow eds.). John Wiley & Sons, New York, USA. 115-176.

Miescher, S. 1999. Antimicrobial and auto-lytic systems of dairy propionibacteria. PhD thesis No. 13486. ETH, Zurich, Switzerland.

Pearson, P. W. R., and D. J. Lipman. 1988. Improved tools for biological sequence comparison. Proc. Natl. Acad. Sci. USA 85: 2444-2448.

Sanger, F., S. Nicklen, and A. R. Coulson. 1977. DNA sequencing with chain-terminating inhibitors. Proc. Natl. Acad. Sci. USA. 74: 5463-5467.

Soumalainen, T. B. and A. M. Märyä-Mäkinen. 1999. Propionic acid bacteria as protective cultures in fermented milks and breads. Lait 79: 165-174.

Vogel, R. P. 1996. Biotechnology of starter organisms for non-dairy lactic food fermentations (Mini-Review). Adv. Food Sci. 18: 46-51.

Ward, L. J. H. and M. J. Timmins. 1999. Differentiation of *Lactobacillus casei, Lactobacillus paracasei* and *Lactobacillus rhamnosus* by polymerase chain reaction. Lett. Appl. Microbiol. 29: 90-92.

Young, J. P. W., H. L. Downer and B. D. Eardly. 1991. Phylogeny of the phototrophic rhizobium strain BTAi1 by polymerase chain reaction-based sequencing of a 16S rRNA gene segment. J. Bacteriol. 173: 2271-2277.

Zusatzstoffverordnung über die in Lebensmitteln zulässigen Zusatzstoffe, vom 26. Juni 1995, Stand am 22. Februar 2000. Eidgenössisches Departement des Innern: Dreifuss. EDMZ, Bern.

DEPOSITED STRAINS

The following strains have been deposited on 18 Sep. 2001 with the DSMZ-Deutsche Sammlung von Mikroorganismen and Zellkulturen GmbH (DSMZ), currently located at Inhoffenstraße 7 B, 38124 Braunschweig, Germany, under the terms of the Budapest Treaty.

Strain *Propionibacterium jensenii* SM11 has been deposited under the number DSM 14513

Strain *Lactobacillus paracasei* subsp. *paracasei* SM20 has been deposited under the number DSM 14514.

Strain *Lactobacillus paracasei* subsp. *paracasei* SM29 has been deposited under the number DSM 14515.

Strain *Lactobacillus paracasei* subsp. *paracasei* SM63 has been deposited under the number DSM 15416.

-continued

| PCT | Original (for SUBMISSION) - printed on 28.10.2002 01:20:47 PM | |
|---|---|---|
| 0-1-1 | Prepared using | PCT-EASY Version 2.92 (updated 01.10.2002) |
| 0-2 | International Application No. | |
| 0-3 | Applicant's or agent's file reference | 05365PC |
| 1 | The indications made below relate to the deposited microorganism(s) or other biological material referred to in the description on: | |
| 1-1 | page | 57 |
| 1-2 | line | 7 |
| 1-3 | Identification of Deposit | |
| 1-3-1 | Name of depositary institution | DSMZ-Deutsche Sammlung von Mikroorganismen und Zellkulturen GmbH |
| 1-3-2 | Address of depositary institution | Mascheroder Weg 1b, D-38124 Braunschweig, Germany |
| 1-3-3 | Date of deposit | 20 Sep. 2001 (20.09.2001) |
| 1-3-4 | Accession Number | DSMZ 14513 |
| 1-4 | Additional Indications | NONE |
| 1-5 | Designated States for Which Indications are Made | all designated States |
| 1-6 | Separate Furnishing of Indications These indications will be submitted to the International Bureau later | NONE |
| 2 | The indications made below relate to the deposited microorganism(s) or other biological material referred to in the description on: | |
| 2-1 | page | 57 |
| 2-2 | line | 10 |
| 2-3 | Identification of Deposit | |
| 2-3-1 | Name of depositary institution | DSMZ-Deutsche Sammlung von Mikroorganismen und Zellkulturen GmbH |
| 2-3-2 | Address of depositary institution | Mascheroder Weg 1b, D-38124 Braunschweig, Germany |
| 2-3-3 | Date of deposit | 20 Sep. 2001 (20.09.2001) |
| 2-3-4 | Accession Number | DSMZ 14514 |
| 2-4 | Additional Indications | NONE |
| 2-5 | Designated States for Which Indications are Made | all designated States |
| 2-6 | Separate Furnishing of Indications These indications will be submitted to the International Bureau later | NONE |
| 3 | The indications made below relate to the deposited microorganism(s) or other biological material referred to in the description on: | |
| 3-1 | page | 57 |
| 3-2 | line | 13 |
| 3-3 | Identification of Deposit | |
| 3-3-1 | Name of depositary institution | DSMZ-Deutsche Sammlung von Mikroorganismen und Zellkulturen GmbH |
| 3-3-2 | Address of depositary institution | Mascheroder Weg 1b, D-38124 Braunschweig, Germany |
| 3-3-3 | Date of deposit | 20 Sep. 2001 (20.09.2001) |
| 3-3-4 | Accession Number | DSMZ 14515 |
| 3-4 | Additional Indications | NONE |
| 3-5 | Designated States for Which Indications are Made | all designated States |
| 3-6 | Separate Furnishing of Indications These indications will be submitted to the International Bureau later | NONE |
| 4 | The indications made below relate to the deposited microorganism(s) or other biological material referred to in the description on: | |
| 4-1 | page | 57 |
| 4-2 | line | 16 |
| 4-3 | Identification of Deposit | |
| 4-3-1 | Name of depositary institution | DSMZ-Deutsche Sammlung von Mikroorganismen und Zellkulturen GmbH |
| 4-3-2 | Address of depositary institution | Mascheroder Weg 1b, D-38124 Braunschweig, Germany |
| 4-3-3 | Date of deposit | 20 Sep. 2001 (20.09.2001) |
| 4-3-4 | Accession Number | DSMZ 15416 |
| 4-4 | Additional Indications | NONE |
| 4-5 | Designated States for Which Indications are Made | all designated States |

-continued

| PCT | Original (for SUBMISSION) - printed on 28.10.2002 01:20:47 PM |
|---|---|
| 4-6 | Separate Furnishing of Indications   NONE<br>These indications will be submitted to<br>the International Bureau later |

FOR RECEIVING OFFICE USE ONLY

| 0-4 | This form was received with the<br>International application:<br>(yes or no) |
|---|---|
| 0-4-1 | Authorized officer |

FOR INTERNATIONAL BUREAU USE ONLY

| 0-5 | This form was received by the<br>International Bureau on: |
|---|---|
| 0-5-1 | Authorized officer |

The invention claimed is:

1. A composition comprising isolated bacteria selected from the group consisting of *Propionibacterium jensenii* SM11 (DSM 14513), *Lactobacillus paracasei* subsp. *paracasei* SM20 (DSM 14514), *Lactobacillus paracasei* subsp. *paracasei* SM29 (DSM 14515) and *Lactobacillus paracasei* subsp. *paracasei* SM63 (DSM 14516), or mixtures thereof.

* * * * *

SEQUENCE LISTING

```
<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: PCR-
      primer

<400> SEQUENCE: 1
tggctcagaa cgaacgctag gcccg                                            25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR-
      primer

<400> SEQUENCE: 2
tgcactgaga ttcgacttaa                                                  20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: PCR-
      primer

<400> SEQUENCE: 3
caccgagatt caacatgg                                                    18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR-
      primer

<400> SEQUENCE: 4
tgcatcttga tttaattttg                                                  20

<210> SEQ ID NO 5
```

```
<211> LENGTH: 19
<212> TYPE: DNA
<213> ORGANISM: Artificial Sequence
<220> FEATURE:
<223> OTHER INFORMATION: Description of Artificial Sequence: PCR-
      primer

<400> SEQUENCE: 5
aggaggtgat ccarccgca                                              19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: PCR-
      primer

<400> SEQUENCE: 6
agtttgatcm tggctcag                                               18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: PCR-
      primer

<400> SEQUENCE: 7
actcctacgg gaggcagc                                               18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: PCR-
      primer

<400> SEQUENCE: 8
accgcggctg ctggcac                                                17

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: PCR-
      primer

<400> SEQUENCE: 9
ggmttagata ccctggtagt cc                                          22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: PCR-
      primer

<400> SEQUENCE: 10
cgttaagtcc cgcaacgagc                                             20

<210> SEQ ID NO 11
<211> LENGTH: 17
<212> TYPE: DNA
```

```
-continued

<213> ORGANISM: Artificial Sequence
<220> FEATURE:
<223> OTHER INFORMATION: Description of Artificial Sequence: PCR-
      primer

<400> SEQUENCE: 11
gtacacaccg cccgtca                                                    17
```